United States Patent
Wong et al.

(10) Patent No.: US 12,202,867 B2
(45) Date of Patent: Jan. 21, 2025

(54) ADENO-ASSOCIATED VIRAL CHIMERIC TDP-43 PROTEINS

(71) Applicant: THE JOHNS HOPKINS UNIVERSITY, Baltimore, MD (US)

(72) Inventors: Philip C. Wong, Baltimore, MD (US); Aneesh Donde, Baltimore, MD (US); Jonathan P. Ling, Baltimore, MD (US); Liam Chen, Baltimore, MD (US); Mingkuan Sun, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 813 days.

(21) Appl. No.: 17/287,730

(22) PCT Filed: Nov. 4, 2019

(86) PCT No.: PCT/US2019/059623
§ 371 (c)(1),
(2) Date: Apr. 22, 2021

(87) PCT Pub. No.: WO2020/093035
PCT Pub. Date: May 7, 2020

(65) Prior Publication Data
US 2022/0275034 A1 Sep. 1, 2022

Related U.S. Application Data

(60) Provisional application No. 62/754,791, filed on Nov. 2, 2018.

(51) Int. Cl.
| C07K 14/47 | (2006.01) |
| A61K 38/00 | (2006.01) |
| C12N 15/86 | (2006.01) |
| C12Q 1/6883 | (2018.01) |

(52) U.S. Cl.
CPC .......... *C07K 14/4702* (2013.01); *C07K 14/47* (2013.01); *C12N 15/86* (2013.01); *C12Q 1/6883* (2013.01); *A61K 38/00* (2013.01); *C12N 2710/10343* (2013.01); *C12N 2840/44* (2013.01); *C12Q 2600/118* (2013.01); *C12Q 2600/156* (2013.01)

(58) Field of Classification Search
CPC ................ C07K 14/4702; C12N 15/86; C12N 2710/10343; C12Q 1/6883
See application file for complete search history.

(56) References Cited

U.S. PATENT DOCUMENTS 3,610,795 A 10/1971 Antoine

FOREIGN PATENT DOCUMENTS

| JP | 2005501127 B2 | 1/2005 | |
| JP | 4279141 B2 | 6/2009 | |
| WO | 2006069610 A3 | 7/2006 | |
| WO | WO-2016205615 A1 * | 12/2016 | ........... A61K 35/761 |

OTHER PUBLICATIONS

Ayala YM, De Conti L, Avendaño-Vazquez SE, Dhir A, Romano M, D'Ambrogio A, Tollervey J, Ule J, Baralle M, Buratti E, Baralle FE. TDP-43 regulates its mRNA levels through a negative feedback loop. EMBO J. Jan. 19, 2011;30(2):277-88. (Year: 2011).*
Sephton, Chantelle F., et al. "TDP-43 is a developmentally regulated protein essential for early embryonic development." Journal of Biological Chemistry 285.9 (2010): 6826-6834.
Taylor, J. Paul, Robert H. Brown, and Don W. Cleveland. "Decoding ALS: from genes to mechanism." Nature 539.7628 (2016): 197-206.
Kabashi, Edor, et al. "TARDBP mutations in individuals with sporadic and familial amyotrophic lateral sclerosis." Nature genetics 40.5 (2008): 572-574.
Renton, Alan E., et al. "A hexanucleotide repeat expansion in C9ORF72 is the cause of chromosome 9p21-linked ALS-FTD." Neuron 72.2 (2011): 257-268.
Salajegheh, Mohammad, et al. "Sarcoplasmic redistribution of nuclear TDP-43 in inclusion body myositis." Muscle & nerve 40.1 (2009): 19-31.
Amador-Ortiz C, Lin WL, Ahmed Z, Personett D, Davies P, Duara R, Graff-Radford NR, Hutton ML, Dickson DW. TDP-43 immunoreactivity in hippocampal sclerosis and Alzheimer's disease. Ann Neurol. May 2007;61(5):435-45. doi: 10.1002/ana.21154. PMID: 17469117; PMCID: PMC2677204.
Ash PE, Zhang YJ, Roberts CM, Saldi T, Hutter H, Buratti E, Petrucelli L, Link CD. Neurotoxic effects of TDP-43 overexpression in C. elegans. Hum Mol Genet. Aug. 15, 2010;19(16):3206-18. doi: 10.1093/hmg/ddq230. Epub Jun. 8, 2010. PMID: 20530643; PMCID: PMC2908471.
Wils, Hans, et al. "TDP-43 transgenic mice develop spastic paralysis and neuronal inclusions characteristic of ALS and frontotemporal lobar degeneration." Proceedings of the National Academy of Sciences 107.8 (2010): 3858-3863.
Yang, Chunxing, et al. "Partial loss of TDP-43 function causes phenotypes of amyotrophic lateral sclerosis." Proceedings of the National Academy of Sciences 111.12 (2014): E1121-E1129.

(Continued)

*Primary Examiner* — Janet L Andres
*Assistant Examiner* — Ruixue Wang
(74) *Attorney, Agent, or Firm* — Tarolli, Sundheim, Covell & Tummino LLP

(57) ABSTRACT

An adenovirus or adenoviral vector is described that includes a non-native nucleotide sequence capable of expressing a chimeric protein comprising an N-terminal nucleotide binding domain of transactivation response element DNA-binding protein (TDP-43), a C-terminal domain derived from a splicing repressor, and an autoregulatory element. Methods of using the adenovirus or adenoviral vector to treat degenerative diseases such as inclusion body myocytosis, amyotrophic lateral sclerosis, and frontotemporal dementia are also described.

10 Claims, 18 Drawing Sheets

Specification includes a Sequence Listing.

(56) References Cited

OTHER PUBLICATIONS

Buratti, Emanuele, et al. "Nuclear factor TDP-43 and SR proteins promote in vitro and in vivo CFTR exon 9 skipping." The EMBO journal 20.7 (2001): 1774-1784.
Freibaum, Brian D., et al. "Global analysis of TOP-43 interacting proteins reveals strong association with RNA splicing and translation machinery." Journal of proteome research 9.2 (2010): 1104-1120.
Ling, Jonathan P., et al. "TDP-43 repression of nonconserved cryptic exons is compromised in ALS-FTD." Science 349.6248 (2015): 650-655.
Sun, Mingkuan, et al. "Cryptic exon incorporation occurs in Alzheimer's brain lacking TDP-43 inclusion but exhibiting nuclear clearance of TDP-43." Acta neuropathologica 133.6 (2017): 923-931.
Ling JP, Chhabra R, Merran JD, Schaughency PM, Wheelan SJ, Corden JL, Wong PC. PTBP1 and PTBP2 Repress Nonconserved Cryptic Exons. Cell Rep. Sep. 27, 2016;17(1):104-113. doi: 10.1016/j.celrep.2016.08.071. PMID: 27681424; PMCID: PMC5082185.
Davis, Leonard. Basic methods in molecular biology. Elsevier, 2012.
Sambrook, J., E. F. Fritsch, and T. Maniatis. "Molecular Cloning. A Laboratory Manual., Second edn. Cold Spring Harbor, NY: Cold Spring Harbor Laboratory Press." (1989).
Yamashita, Takenari, et al. "Rescue of amyotrophic lateral sclerosis phenotype in a mouse model by intravenous AAV 9-ADAR 2 delivery to motor neurons." EMBO molecular medicine 5.11 (2013): 1710-1719.
Ginsberg, H. S., et al. "A proposed terminology for the adenovirus antigens and virion morphological subunits." Virology 28.4 (1966): 782-3.
Roberts, Michael M., et al. "Three-dimensional structure of the adenovirus major coat protein hexon." Science 232.4754 (1986): 1148-1151.
Stewart, Phoebe L., et al. "Image reconstruction reveals the complex molecular organization of adenovirus." Cell 67.1 (1991): 145-154.
Curiel, David T., et al. "High-efficiency gene transfer mediated by adenovirus coupled to DNA-polylysine complexes." Human Gene Therapy 3.2 (1992): 147-154.
Cohen, Todd J., Virginia MY Lee, and John Q. Trojanowski. "TDP-43 functions and pathogenic mechanisms implicated in TDP-43 proteinopathies." Trends in molecular medicine 17.11 (2011): 659-667.
Hancks DC, Kazazian HH Jr. Active human retrotransposons: variation and disease. Curr Opin Genet Dev. Jun. 2012;22(3):191-203. doi: 10.1016/j.gde.2012.02.006. Epub Mar. 8, 2012. PMID: 22406018; PMCID: PMC3376660.
Baugh CM, Stamm JM, Riley DO, Gavett BE, Shenton ME, Lin A, Nowinski CJ, Cantu RC, McKee AC, Stem RA. Chronic traumatic encephalopathy: neurodegeneration following repetitive concussive and subconcussive brain trauma. Brain Imaging Behav. Jun. 2012;6(2):244-54. doi: 10.1007/s11682-012-9164-5. PMID: 22552850.
Uryu, Kunihiro, et al. "Concomitant TAR-DNA-binding protein 43 pathology is present in Alzheimer disease and corticobasal degeneration but not in other tauopathies." Journal of Neuropathology & Experimental Neurology 67.6 (2008): 555-564.
Ayala, Youhna M., et al. "TDP-43 regulates its mRNA levels through a negative feedback loop." The EMBO journal 30.2 (2011): 277-288.
Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.
Chen, Michael Y., et al. "Surface properties, more than size, limiting convective distribution of virus-sized particles and viruses in the central nervous system." Journal of neurosurgery 103.2 (2005): 311-319.
Fu, Xinping, et al. "Expression of a fusogenic membrane glycoprotein by an oncolytic herpes simplex virus potentiates the viral antitumor effect." Molecular Therapy 7.6 (2003): 748-754.

Foust KD, Wang X, McGovern VL, Braun L, Bevan AK, Haidet AM, Le TT, Morales PR, Rich MM, Burghes AH, Kaspar BK. Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010. PMID: 20190738; PMCID: PMC2889698.
Rideau, Alexis P., et al. "A peptide motif in Raver1 mediates splicing repression by interaction with the PTB RRM2 domain." Nature structural & molecular biology 13.9 (2006): 839-848.
Feiguin, Fabian, et al. "Depletion of TDP-43 affects Drosophila motoneurons terminal synapsis and locomotive behavior." FEBS letters 583.10 (2009): 1586-1592.
Rossi J, Balthasar N, Olson D, Scott M, Berglund E, Lee CE, Choi MJ, Lauzon D, Lowell BB, Elmquist JK. Melanocortin-4 receptors expressed by cholinergic neurons regulate energy balance and glucose homeostasis. Cell Metab. Feb. 2, 2011;13(2):195-204. doi: 10.1016/j.cmet.2011.01.010. PMID: 21284986; PMCID: PMC3033043.
Iguchi Y, Katsuno M, Niwa J, Takagi S, Ishigaki S, Ikenaka K, Kawal K, Watanabe H, Yamanaka K, Takahashi R, Misawa H, Sasaki S, Tanaka F, Sobue G. Loss of TDP-43 causes age-dependent progressive motor neuron degeneration. Brain. May 2013;136(Pt 5):1371-82. doi: 10.1093/brain/awt029. Epub Feb. 28, 2013. PMID: 23449777.
Polymenidou M, Lagier-Tourenne C, Hutt KR, Huelga SC, Moran J, Liang TY, Ling SC, Sun E, Wancewicz E, Mazur C, Kordasiewicz H, Sedaghat Y, Donohue JP, Shiue L, Bennett CF. Yeo GW, Cleveland DW. Long pre-mRNA depletion and RNA missplicing contribute to neuronal vulnerability from loss of TDP-43. Nat Neuroscl. Apr. 2011;14(4):459-68. doi: 10.1038/nn.2779. Epub Feb. 27, 2011. PMID: 21358643; PMCID: PMC3094729.
Kawamoto S, Shi Q, Nitta Y, Miyazaki J, Allen MD. Widespread and early myocardial gene expression by adeno-associated virus vector type 6 with a beta-actin hybrid promoter. Mol Ther. Jun. 2005;11(6):980-5. doi: 10.1016/j.ymthe.2005.02.009. PMID: 15922969.
Jeong YH, Ling JP, Lin SZ, Donde AN, Braunstein KE, Majounie E, Traynor BJ, LaClair KD, Lloyd TE, Wong PC. TDP-43 cryptic exons are highly variable between cell types. Mol Neurodegen. Feb. 2, 2017;12(1):13. doi: 10.1186/s13024-016-0144-x. PMID: 28153034; PMCID: PMC5289002.
Chan KY, Jang MJ, Yoo BB, Greenbaum A, Ravi N, Wu WL, Sánchez-Guardado L, Lois C, Mazmanian SK, Deverman BE, Gradinaru V. Engineered AAVs for efficient noninvasive gene delivery to the central and peripheral nervous systems. Nat Neurosci. Aug. 2017;20(8):1172-1179. doi: 10.1038/nn.4593. Epub Jun. 26, 2017. PMID: 28671695; PMCID: PMC5529245.
Ling JP, Pletnikova O, Troncoso JC, Wong PC. TDP-43 repression of nonconserved cryptic exons is compromised in ALS-FTD. Science. Aug. 7, 2015;349(6248):650-5. doi: 10.1126/science.aab0983. PMID: 26250685; PMCID: PMC4825810.
White MA, Kim E, Duffy A, Adalbert R, Phillips BU, Peters OM, Stephenson J, Yang S, Massenzio F, Lin Z, Andrews S, Segonds-Pichon A, Metterville J, Saksida LM, Mead R, Ribchester RR, Barhomi Y, Serre T, Coleman MP, Fallon JR, Bussey TJ, Brown RH Jr, Sreedharan J. TDP-43 gains function due to perturbed autoregulation in a Tardbp knock-in mouse model of ALS-FTD. Nat Neurosci. Apr. 2018;21(4):552-563. doi: 10.1038/s41593-018-0113-5. Epub Mar. 19, 2018. Erratum in: Nat Neurosci. Aug. 2018;21(8):1138. PMID: 29556029; PMCID: PMC5884423,.
Becker LA, Huang B, Bieri G, Ma R, Knowles DA, Jafar-Nejad P, Messing J, Kim HJ, Soriano A, Auburger G, Pulst SM, Taylor JP, Rigo F, Giller AD. Therapeutic reduction of ataxin-2 extends lifespan and reduces pathology in TDP-43 mice. Nature. Apr. 20, 2017;544(7650):367-371. doi: 10.1038/nature22038. Epub Apr. 1, 20172. PMID: 28405022; PMCID: PMC5642042.
Kim HJ, Raphael AR, LaDow ES, McGurk L, Weber RA, Trojanowski JQ, Lee VM, Finkbeiner S, Gitler AD, Bonini NM. Therapeutic modulation of elF2α phosphorylation rescues TDP-43 toxicity in amyotrophic lateral sclerosis disease models. Nat Genet. Feb. 2014;46(2):152-60. doi: 10.1038/ng.2853. Epub Dec. 15, 2013. PMID: 24336168; PMCID: PMC3934366.
Neumann, Manuela, et al. "Ubiquitinated TDP-43 in frontotemporal lobar degeneration and amyotrophic lateral sclerosis." Science 314.5796 (2006): 130-133.

(56) References Cited

OTHER PUBLICATIONS

Sreedharan, Jemeen, et al. "TDP-43 mutations in familial and sporadic amyotrophic lateral sclerosis." Science 319.5870 (2008): 1668-1672.
Cox FM, Titulaer MJ, Sont JK, Wintzen AR, Verschuuren JJ, Badrising Ua. A 12-year follow-up in sporadic inclusion body myositis: an end stage with major disabilities. Brain. Nov. 2011;134(Pt 11):3167-75. doi: 10.1093/brain/awr217. Epub Sep. 9, 2011. PMID: 21908393.
Lloyd TE. Novel therapeutic approaches for inclusion body myositis. Curr Opin Rheumatol. Nov. 2010;22(6):658-64. doi: 10.1097/BOR.0b013e32833f0f4a. PMID: 20827206; PMCID: PMC4365473.
Chiang PM, Ling J, Jeong YH, Price DL, Aja SM, Wong PC. Deletion of TDP-43 down-regulates Tbc1d1, a gene linked to obesity, and alters body fat metabolism. Proc Natl Acad Sci U S A. Sep. 14, 2010;107(37):16320-4. doi: 10.1073/pnas.1002176107. Epub Jul. 26, 2010. PMID: 20660762; PMCID: PMC2941284.
Mourkioti F, Slonimsky E, Huth M, Berno V, Rosenthal N. Analysis of CRE-mediated recombination driven by myosin light chain 1/3 regulatory elements in embryonic and adult skeletal muscle: a tool to study fiber specification. Genesis. Aug. 2008;46(8):424-30. doi: 10.1002/dvg.20419. PMID: 18693277.
Askanas V, Engel WK. Sporadic inclusion-body myositis and hereditary inclusion-body myopathies: current concepts of diagnosis and pathogenesis. Curr Opin Rheumatol. Nov. 1998;10(6):530-42. doi: 10.1097/00002281-199811000-00005. PMID: 9812213.
Salajegheh M, Pinkus JL, Taylor JP, Amato AA, Nazareno R, Baloh RH, Greenberg SA. Sarcoplasmic redistribution of nuclear TDP-43 in inclusion body myositis. Muscle Nerve. Jul. 2009;40(1): 19-31. doi: 10.1002/mus.21386. PMID: 19533646; PMCID: PMC2700211.
Kim, Hong Joo, et al. "Mutations in prion-like domains in hnRNPA2B1 and hnRNPA1 cause multisystem proteinopathy and ALS." Nature 495.7442 (2013): 467-473.
Pinkus, Jack L., et al. "Abnormal distribution of heterogeneous nuclear ribonucleoproteins in sporadic inclusion body myositis." Neuromuscular Disorders 24.7 (2014): 611-616.
Trapnell, Cole, et al. "Differential gene and transcript expression analysis of RNA-seq experiments with TopHat and Cufflinks." Nature protocols 7.3 (2012): 562-578.
Pertea, Mihaela, et al. "StringTie enables improved reconstruction of a transcriptome from RNA-seq reads." Nature biotechnology 33.3 (2015): 290-295.
International Search Report for Corresponding Application Serial No. PCT/US2019/59623.
European Search Report for Corresponding Application Serial No. PCT/US2019/59623.
Fiesel FC, Kahle PJ. TDP-43 and FUS/TLS: cellular functions and implications for neurodegeneration. FEBS J. Oct. 2011;278(19):3550-68. doi: 10.1111/j.1742-4658.2011.08258.x. Epub Aug. 24, 2011. PMID: 21777389.

* cited by examiner

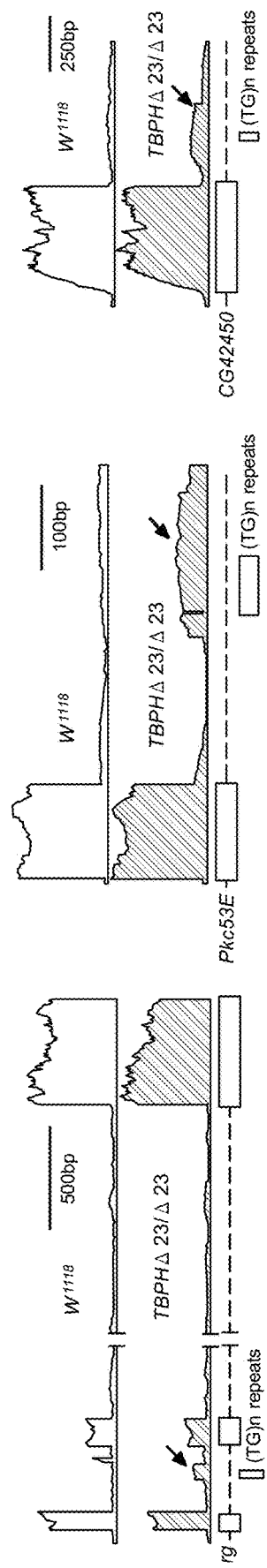
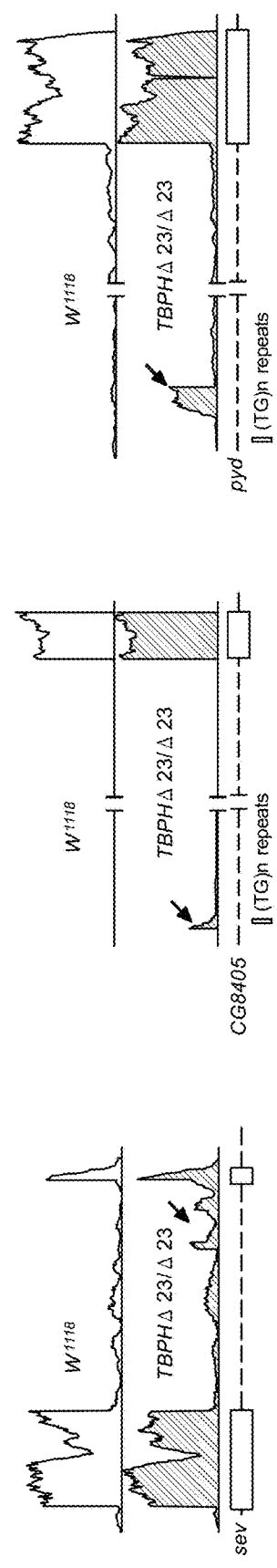

| Gene | Genomic Sequence |
|---|---|
| rg | cttgttggttgagacg tgtgtgtatgt...atgtgtga... atgtgtgtgagtgtgtgc... gccaacgaaaacaaaaaaaaacaaaactaa |
| CG8405 | tattgatgcggatacttcgggttactcgg tgtgtgtgtgtgtgtgcacacaatcaa ctcgaattaaattcaataacataactcaatcatg |
| Dyb | ttggcagatgctcatgcg...ttcgccccgtgcccaagaattgtgagtg ctagtgcgagaacgagtgatgagtgggtgagtg... ctgttgttgctct |
| Pkc53E | aaaaaaaaacacccgactgacagtgtaaa taatgatgataatgtgcgtgagtgtgtgtgtgtgagtgtctg... catacatgtaagcaggccgc |
| CG42450 | gtagcaa...tgtttgtg tgcg...tgtga... tgtgtgtgtt tgtgggagtg tgtgctgc...ttggtgt gtgtgctgtg gtgtggtgt g...cccactggg |

-----5'-intron upstream----- | Cryptic exon ...Cryptic exon | -----3'-intron upstream-----

FIG. 1G

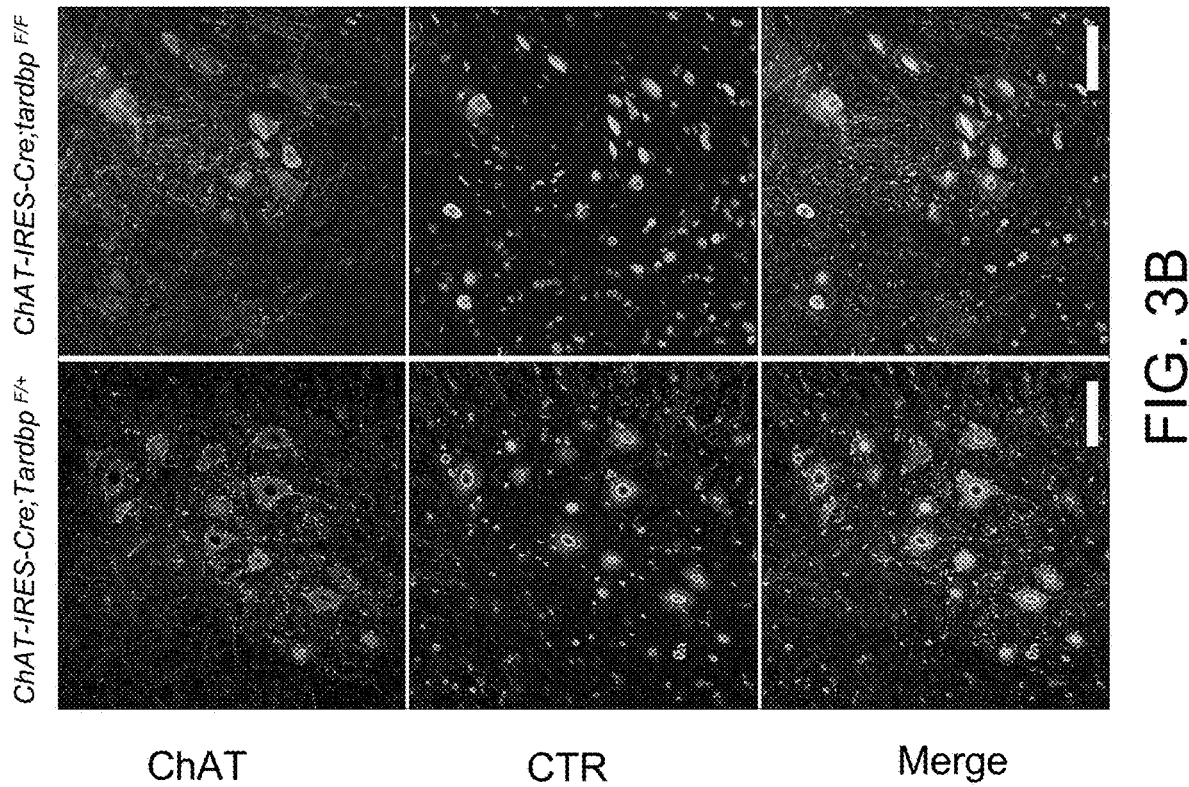
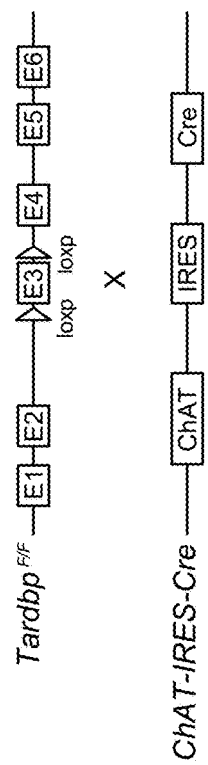
FIG. 3B
ChAT    CTR    Merge
FIG. 3A

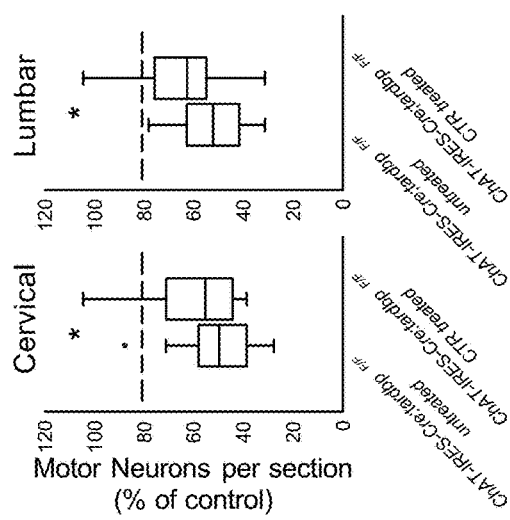
FIG. 5B
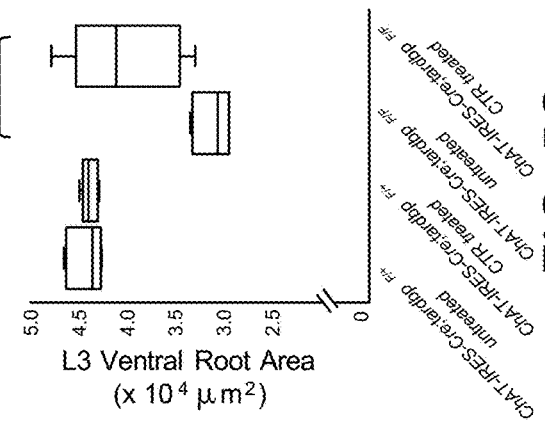
FIG. 5C
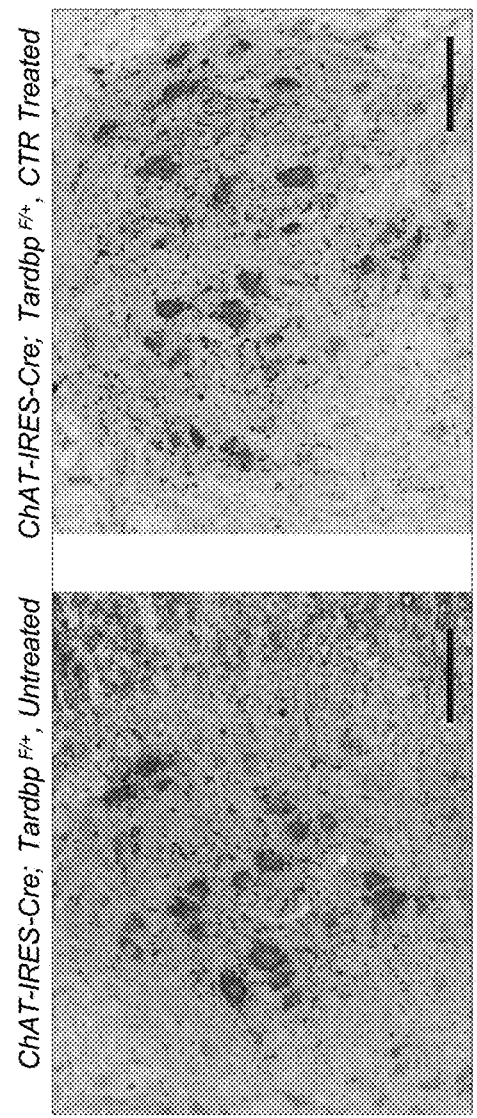
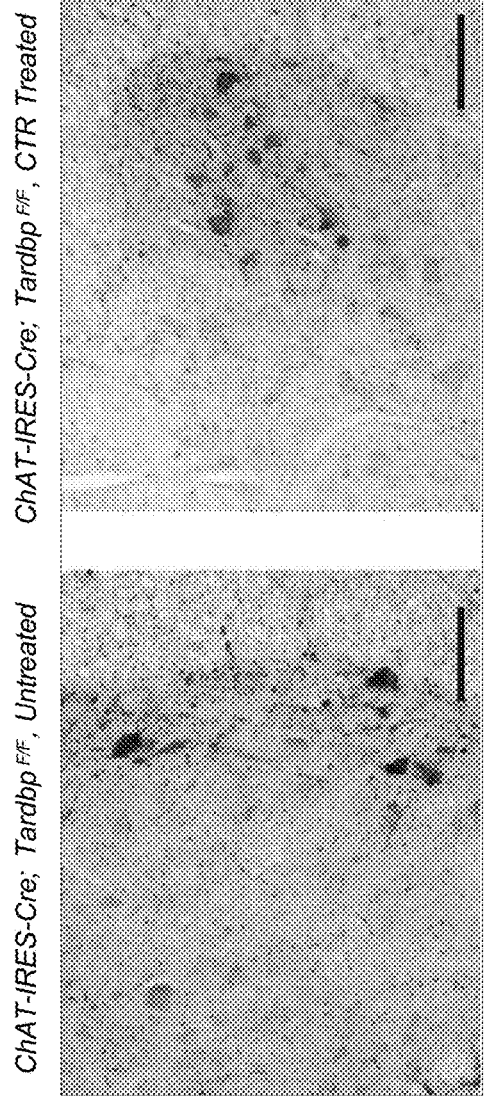
FIG. 5A

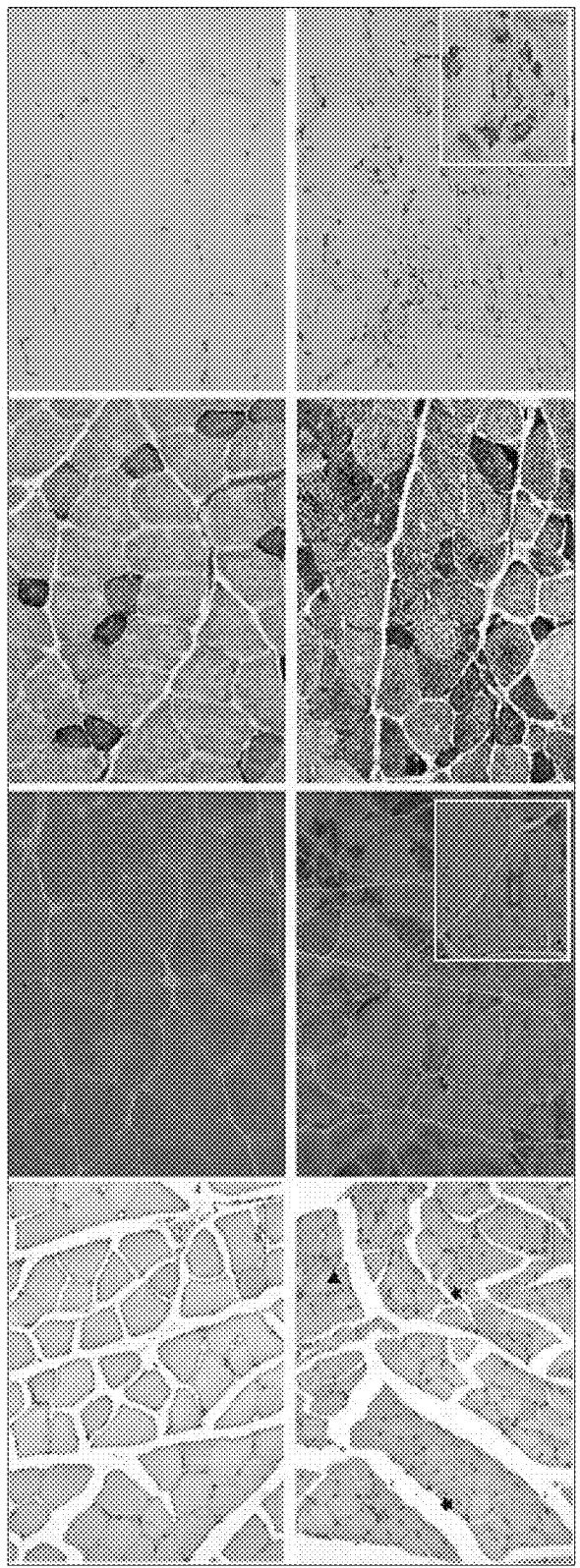
FIG. 7D
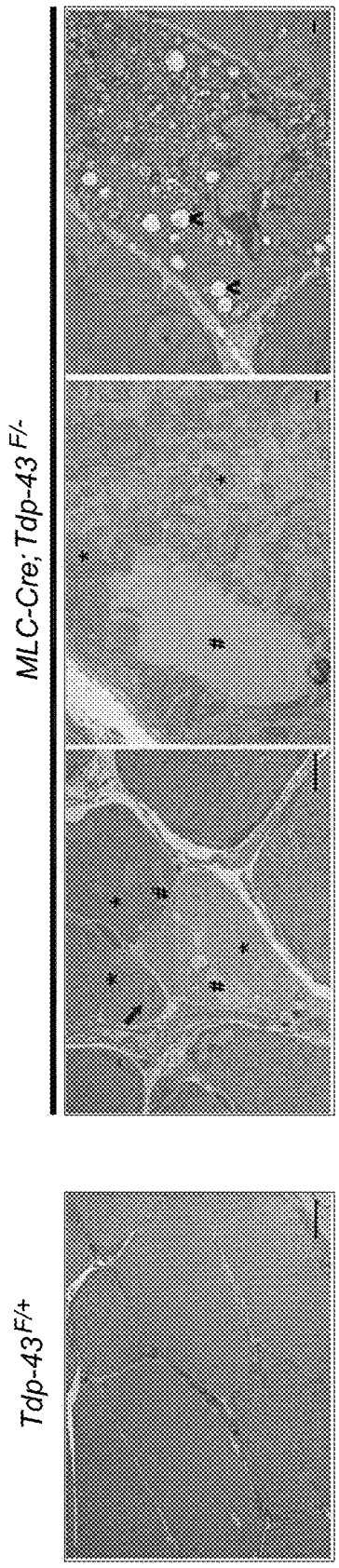
FIG. 7F
FIG. 7E

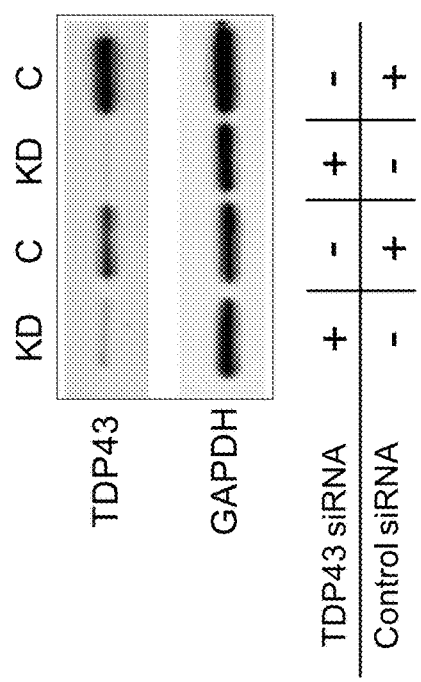
FIG. 8A
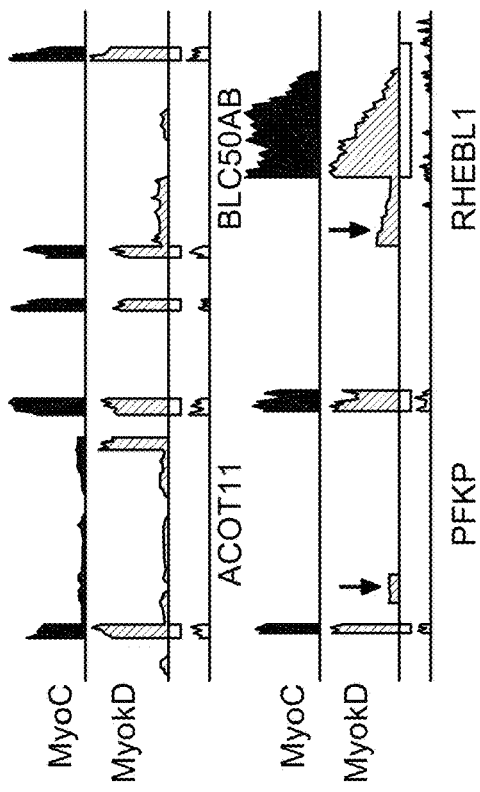
FIG. 8B
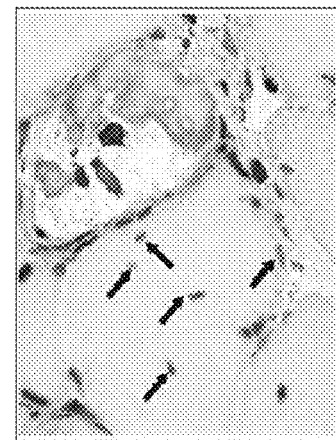
FIG. 8F
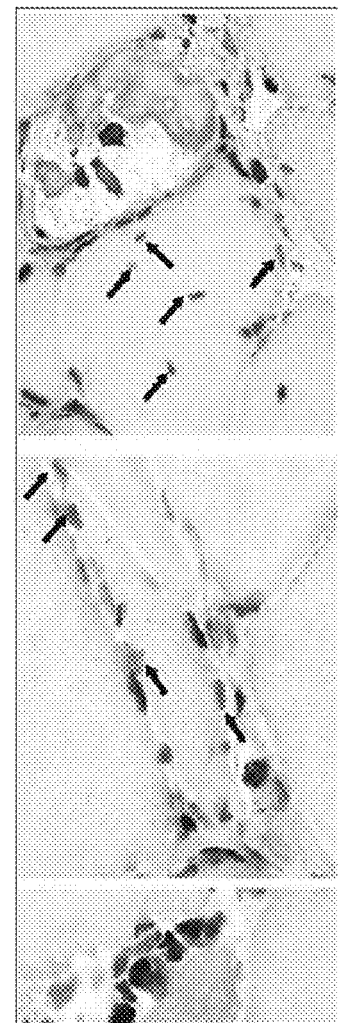
FIG. 8E
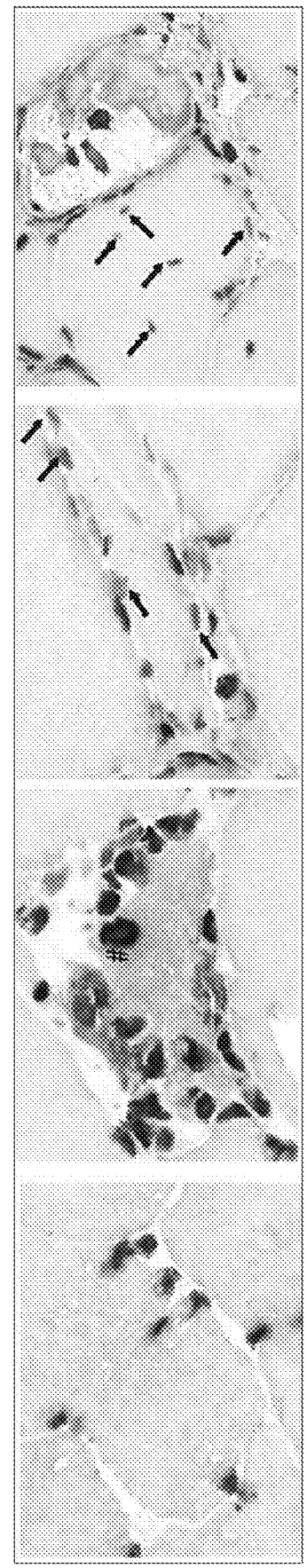
FIG. 8D
FIG. 8C

ADENO-ASSOCIATED VIRAL CHIMERIC TDP-43 PROTEINS

CROSS-REFERENCE TO RELATED APPLICATIONS

This application claims priority to U.S. Provisional Patent Application Ser. No. 62/754,791, filed 2 Nov. 2018, all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 9, 2019, is named JHU-027719_WO_ORD_SL.txt and is 24,112 bytes in size.

GOVERNMENT FUNDING

This invention was made with government support under grant no. NS095969 awarded by the National Institutes of Health. The government has certain rights in this invention.

BACKGROUND

Tar DNA-binding protein 43 (TDP-43, encoded by the gene TARDBP), an essential, highly-conserved RNA binding protein (C. F. Sephton et al., 285, 6826 (2010)), has been implicated in amyotrophic lateral sclerosis (ALS), a progressive neurodegenerative disease characterized by the death of upper and lower motor neurons. In nearly all cases of sporadic ALS, TDP-43 in motor neurons depletes from the nucleus and aggregates in the cytoplasm. Taylor et al., Nature, 539, 197 (2016). Missense mutations in TDP43, which mostly cluster within its C-terminal domain, are linked to familial ALS (Kabashi et al., Nat. Genet., 40, 572 (2008)), and various other genetic mutations associated with familial ALS are also associated with TDP43 pathology, supporting the notion that TDP-43 mislocalization is central to its pathogenesis. A. E. Renton et al., Neuron, 72, 257 (2011). In addition, TDP-43 pathology is evident in cases with frontotemporal dementia (Neuman et al., Science, 314, 130 (2006)), inclusion body myositis (M. Salajegheh et al., Muscle Nerve 40, 19 (2009)), and Alzheimer's disease (C. Amador-Ortiz et al., Ann. Neurol. 61, 435 (2007)). However, the precise mechanism underlying TDP-43 pathology remains unclear. While initial efforts focused on studies of transgenic wild-type human and ALS-linked mutant human TDP-43 overexpression models (P. E. Ash et al., Hum. Mol. Genet. 19, 3206 (2010); H. Wils et al., P.N.A.S. USA, 107, 3858 (2010)), subsequent research suggests that loss of nuclear TDP-43 function plays a critical role in motor neuron degeneration. C. Yang et al., P.N.A.S. USA, 111, E1121 (2014).

TDP-43 is thought to play important roles in several essential cellular processes, including cellular stress response pathways, mRNA delivery to dendritic or axonal compartments, or phase separation of membrane-less organelles. As a member of the heterogeneous ribonuclear protein (hnRNP) family, nuclear TDP-43 is concentrated in transcriptionally-active euchromatin regions, and is thought to regulate alternative splicing. E. Buratti et al., Embo J. 20, 1774 (2001). TDP-43 interacts with many proteins and RNAs, potentially regulating numerous pathways and complicating efforts at developing mechanism-based therapies. B. D. Freibaum et al., J. of Proteome Research, 9, 1104 (2010). Previously, we discovered that TDP-43 acts as a guardian of the transcriptome by repressing the splicing of nonconserved, unannotated 'cryptic' exons (J. P. Ling et al., Science, 349, 650 (2015)), a function that is compromised in cases of neurodegenerative diseases with TDP-43 pathology. M. Sun et al., Acta Neuropathol., 133, 923 (2017). However, since TDP-43 is involved in multiple other intracellular roles, it remains unknown whether splicing repression is an essential function of TDP-43 in motor neurons.

SUMMARY OF THE INVENTION

Nuclear depletion of TDP-43, an RNA binding protein which represses aberrant splicing, may underlie neurodegeneration in amyotrophic lateral sclerosis (ALS). As multiple functions are ascribed to TDP-43, its major role(s) in motor neurons that may be compromised in ALS remains unknown. Using *Drosophila* and murine models lacking TDP43 in motor neurons, we show that TDP-43 mediated splicing repression is central to motor neuron physiology. Employing an AAV9 approach to deliver a chimeric protein comprised of the RNA recognition domain of TDP-43 fused to an unrelated splicing repressor (RAVER1), we validate TDP-43 splicing repression in the motor neuron as a therapeutic target. We establish that splicing repression is a principal role of TDP-43 in the motor neuron and identify for ALS a novel mechanism-based therapeutic strategy.

The inventors also show that mice lacking TDP-43 in skeletal muscle develop an age-dependent myopathy exhibiting key pathological features of IBM. Depletion of TDP-43 from human myoblasts leads to a failure in repressing nonconserved cryptic exons. Immunocytochemical and RNA-seq analysis, respectively, of IBM muscle biopsies reveals the nuclear clearance of TDP-43 and incorporation of nonconserved cryptic exons, respectively. Using a panel of human TDP-43 nonconserved cryptic exon targets, we developed a diagnostic prognostic molecular biomarker for IBM. These data establish that TDP-43 repression of cryptic exons is compromised in IBM, suggesting for this enigmatic muscle disease of older adults a novel therapeutic strategy and biomarker.

BRIEF DESCRIPTION OF THE FIGURES

The present invention may be more readily understood by reference to the following figures, wherein:

FIGS. 1A-1G provide graphs and images showing cryptic exon incorporation in TBPH-deficient flies. Visualization of the cryptic exons (arrows) located in representative genes (red bar). Gene annotation is shown below, labeling exons (thick) and introns (dashed). Cryptic exons may have standard 5' and 3' splice sites [rg, (A) and Pkc53E, (B)], or it may present as exon extension [CG42450, (C)], 5' untranslated region [sev, (D)], polyadenylation site [CG8405, (E)], or inframe insertion [pyd (F)]. (G) Cryptic exons are flanked by UG tandem repeats that exist upstream, downstream, or internally.

FIGS. 3A-3D provide graphs and images showing the expression of CTR in Tdp-43 knockout mice. (A) Schematic of ChAT-IRES-Cre and Tardbp$^{F/F}$ alleles in our conditional Tdp-43 knockout mouse. Cre-mediated excision of exon 3 leads to nonsense-mediated decay of the mRNA transcript. (B) Immunostaining of ChAT (red) and CTR (recognized by human-specific N-terminal TDP-43 antibody, green) in representative lumbar ventral horn sections of ChAT-IRES-Cre; Tardbp$^{F/+}$ and ChAT-IRESCre;Tardbp$^{F/F}$ mice. (C) Quantification of nuclear CTR in ChAT-positive neurons in ChATIRES-Cre;Tardbp$^{F/+}$ mice in cervical (green), lumbar (red), and dorsal horn neurons (blue). Our protocol allowed for a ~60% efficiency of targeting motor neurons until at least 8 months, with no difference observed between cervical and lumbar regions. (N=3 animals 10 per time point, 5 spinal sections per region per animal, scale bar=100 μm). (D) Diagram of the CTR chimeric protein construct packaged in AAV9, with the N-terminal fragment of human TDP-43 (orange), the splicing repression domain of RAVER1 (blue), and the 3' untranslated region (3'UTR) from human TDP-43.

FIGS. 5A-5E provides graphs and images showing expression of CTR in Tdp-43 knockout mice attenuates motor neuron loss and restores splicing repression. (A) Representative ChAT immunostaining of an L3 lumbar ventral horn section at 3 months' age. (scale bar=100 μm). (B) Quantification of ChAT-positive motor neurons in CTR-treated (blue) and untreated (red) knockout mice at 3 months' age. As no difference was observed between CTR-treated and untreated ChAT-IRES-Cre;Tardbr$^{F/+}$ mice, results are shown as a percentage of each group's respective control. Untreated knockout mice showed a 50% decrease in motor neuron number at p90, whereas the motor neuron abundance of CTR-treated knockout mice is 63% (lumbar) and 61% (cervical) of controls (*p<0.05). With our observed transduction efficiency of 60 percent, a complete cell-autonomous rescue of motor neuron death by CTR would still only result in a motor neuron rescue of ~80% (dashed line). (C,D) Representative cresyl violet stained dorsal and ventral L3 root sections and quantification of cross-sectional area. Ventral, but not dorsal, root area was diminished in untreated ChAT-IRES-Cre;Tardbp$^{F/F}$ mice and restored with CTR treatment (scale bar=200 μm). (E) Relative levels of cryptic exon mRNA targets predicted to be incorporated in Tdp-43 deficient motor neurons in p45 mice, normalized to an average of GAPDH and TBP genes as determined by quantitative RT-PCR. A reduction in cryptic exon incorporation in all three tested targets was observed in CTR-treated ChAT-IRES-Cre;Tardbp$^{F/F}$ mice, indicating a partial restoration of splicing repression (* p<0.05).

FIGS. 7A-7F provide images showing conditional knockout of Tdp-43 in skeletal muscle leads to an IBM-like mouse model. A) Levels of Tdp-43 was substantially reduced in skeletal muscle of MLC-Cre;Tdp-43$^{F/−}$ mice (cKO) compared to Tdp-43$^{F/+}$ control mice (C). C) Median survival of MLC-Cre;Tdp-43$^{F/−}$ mice (K) was 130 days, control littermates (C) survived well past the span of the experiment (p<0.0001). D) Immunohistochemical stainings of quadriceps show pathological changes in MLC-Cre;Tdp-43$^{F/−}$ mice (lower panels) compared to control Tdp-43$^{F/+}$ mice (upper panels). (H&E first panel, Gomori Trichrome second panel, NADH third panel, p62 staining fourth panel) These changes have features that resemble that of Inclusion Body Myopathy (refer to text for detailed description). Error bars represent 50 μm. E) Myocytes of Tdp-43$^{F/+}$ mice have regular banding pattern with peripherally located nuclei and morphologically normal mitochondria located adjacent to Z-disks. F) Myocytes of MLCCre;Tdp-43$^{F/−}$ mice have disintegrated myofilament (loss of banding pattern) with amorphous sarcoplasmic deposits (#), redistribution of mitochondria (*) and aberrant nuclei (→) (left panel). Accumulation of swollen degenerate mitochondria (*) around sarcoplasmic inclusions (#) were common (middle panel). Accumulation of vacuole-like structures (>) within myofibers of MLC-Cre;Tdp-43$^{F/−}$ mice (right panel). Error bars represent 10 μm (E-F left panel) and 500 nm (F middle and right panel).

FIGS. 8A-8H provide images showing development of a biomarker for IBM. A) Levels of TDP-43 was substantially reduced in myoblasts treated with TDP-43 siRNA (KD) compared to control siRNA (C). B) Visualization of the cryptic exons (green arrow) in myoblast cells with TDP-43 knockdown (MyoKD) compared to control myoblasts (MyoC): ACOT11, SLC39AB, PFKP, and RHEBL1. C-F) Immunohistochemical TDP-43 staining of muscle sections. C) control muscle showing TDP-43 staining in the nucleus. D) Accumulations of TDP-43 in the cytoplasm (#) E-F) nuclear clearing of TDP-43 in all IBM cases (→). G) Visualization of the cryptic exons (green arrow) in MyoKD, MyoC, Dermatomyositis (DM), mild, nonspecific atrophy (C1), and IBM cases: GPSM2, ACSF2, HDGFRP2, and ZFP91. H) DNA fragments are detected at 199 base pairs (bp) (GPSM2) and at 215 bp (ATG4B) for all cases that display TDP-43 proteinopathy; control cases do not display these fragments. Cases 2, 4, 10, 12, 13, 14, 15, and 18 are IBM and showed nuclear clearing of TDP-43, cases 1, 7, 8, and 9 are Dermatomyositis (DM), cases 5 and 11 are neurogenic atrophy (NA), case 6, 16 and 17 are normal or mild nonspecific (C).

DETAILED DESCRIPTION OF THE INVENTION

Figure 2B:
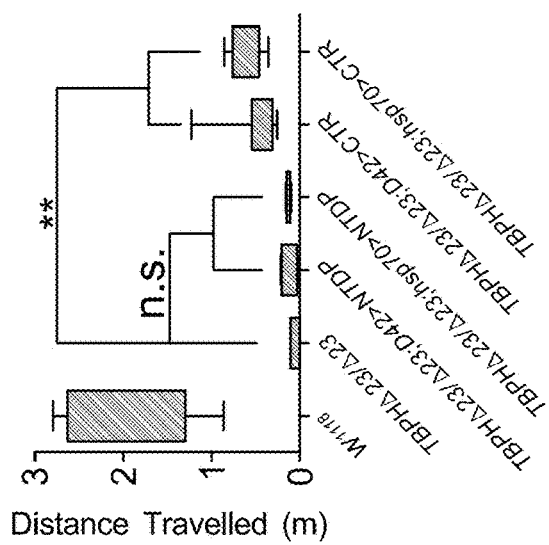
FIGS. 2A-2E provide graphs and images showing the expression of CTR in TBPH-deficient flies. (a) Diagram of the UAS-CTR and UAS-NTDP chimeric constructs. (b) Diagram showing that expression of CTR fusion protein rather than NTDP could significantly ameliorate locomotive function. (c) Graph showing that expression of CTR fusion protein rather than NTDP could significantly extend lifespan. (d) Diagram showing that expression of CTR fusion protein rather than NTDP significantly increased synaptic boutons. (e) An image showing that expression of CTR fusion protein rather than NTDP could significantly repress a variety of cryptic exons including standard cassette (rg), 5' untranslated region (sev), transcriptional start site (Dyb) and exon extension (Syn) in a homozygous TBPH$^{\Delta23}$ null background. ( p<0.01, * p<0.001).
Figure 2A:
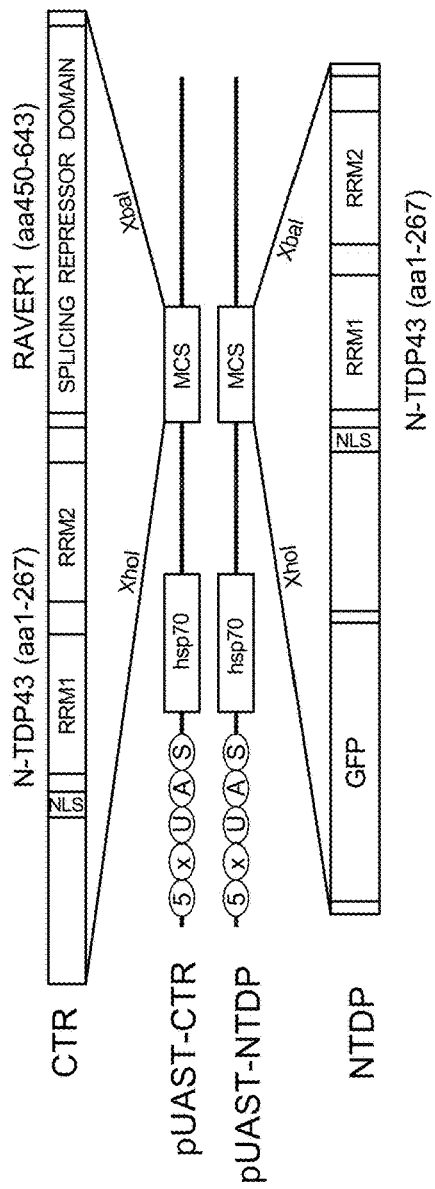

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the terms "treat," "treatment," "treating" include: (i) prophylactic treatment, which includes preventing and/or reducing the incidence of and/or ameliorating the effect and/or duration of a disease, disorder, or condition from occurring in subjects that may get, be exposed to and/or be predisposed to the disease, disorder or condition, but may not yet have been diagnosed as having it; or are diagnosed as having the disease, disease, or condition; or are at risk of developing such disease, disorder, or condition; (ii) inhibiting the disease, disorder, or condition, i.e., delaying the onset of a disease, disorder, or condition; arresting further development or progression of a disease, disorder, or condition in a subject already suffering from or having one or more symptoms of the disease, disorder, or condition; or reducing the risk of a disease, disorder, or condition worsening; (iii) relieving the disease, disorder, or condition, i.e., causing regression of the disease, disorder, or condition, or one or more of its symptoms.

The term "diagnosis" refers to a relative probability that a disease manifesting TDP-43 dysfunction or dysregulation is present in the subject. Similarly, the term "prognosis" refers to a relative probability that a certain future outcome may occur in the subject. For example, in the context of the present invention, prognosis can refer to the likelihood that an individual will develop a disease manifesting TDP-43 dysfunction or dysregulation, or the likely severity of the disease (e.g., severity of symptoms, rate of functional decline, survival, etc.). The terms are not intended to be absolute, as will be appreciated by any one of skill in the field of medical diagnostics.

A "subject," as used herein, can be any animal, and may also be referred to as the patient. Preferably the subject is a mammal, such as a research animal (e.g., a monkey, rabbit, mouse or rat) or a domesticated farm animal (e.g., cow, goat, horse, pig) or pet (e.g., dog, cat). In some embodiments, the subject is a human.

The term "therapeutically effective" is intended to qualify the amount of each protein or nucleic acid that will achieve the goal of decreasing disease severity while avoiding adverse side effects such as those typically associated with alternative therapies. As is well known in the medical arts, dosage for any one animal or human depends on many factors, including the subject's size, body surface area, age, the particular composition to be administered, sex, time and route of administration, general health, and other drugs being administered concurrently. Specific dosages of proteins and nucleic acids can be determined readily determined by one skilled in the art. A therapeutically effective amount may be administered in one or more doses.

As used herein the term "nucleic acid" or "oligonucleotide" refers to multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Other such modifications are well known to those of skill in the art. Thus, the term nucleic acid also encompasses nucleic acids with substitutions or modifications, such as in the bases and/or sugars.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

As used herein, the terms "peptide," "polypeptide" and "protein" are used interchangeably, and refer to a compound comprised of amino acid residues covalently linked by peptide bonds. A protein or peptide must contain at least four amino acids, unless specified otherwise, and no limitation is placed on the maximum number of amino acids that can comprise the sequence of a protein or peptide. Polypeptides include any peptide or protein comprising four or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, 5th ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

All scientific and technical terms used in the present application have meanings commonly used in the art unless otherwise specified. The definitions provided herein are to facilitate understanding of certain terms used frequently herein and are not meant to limit the scope of the present application.

Adenoviral Chimeric TDP-43

In one aspect, the present invention provides an adenovirus or adenoviral vector that includes a non-native nucleotide sequence capable of expressing a chimeric protein comprising an N-terminal nucleotide binding domain of transactivation response element DNA-binding protein (TDP-43), a C-terminal domain derived from a splicing repressor, and an autoregulatory element.

The adenovirus or adenoviral vector can further comprise a non-native nucleotide sequence (i.e., a transgene). The non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The non-native nucleic acid sequence preferably is DNA and encodes a chimeric TDP-43 protein.

TransActivation Response element-DNA binding protein-43 (TDP-43) is an RNA binding protein containing two RNA-recognition motifs (RRM), a nuclear localization signal (NLS), a nuclear export signal (NES), as well as a C-terminal glycine-rich domain (GRD) implicated in TDP-43 protein interactions and functions. The protein is normally concentrated in the nucleus but also shuttles back and forth between the nucleus and cytoplasm. Human TDP-43 is described by NCBI Protein Reference Sequence NP_021401.1. The N-terminal region of TDP-43 includes amino acids 1-268, and has the amino acid sequence:

MSEYIRVTEDENDEPIEIPSEDDGTVLLSTVTAQFP-GACGLRYRNPVSQCMRG VRLVEGILHAP-DAGWGNLVYVVNYPKDNKRKMDETDAS-SAVKVKRAVQKTSDLIV
LGLPWKTTEQDLKEYFSTFGEVLMVQVKKDLKTGH-SKGFGFVRFTEYETQVKVMS MIDGRWCDCK-LPNSKQSQDEPLRSRKVFVGRCTEDMTEDELREFF-SQYGDVMDV
FIPKPFRAFAFVTFADDQIAQSLCGEDLIIKGISVHIS-NAEPKHNSNRQRH (SEQ ID NO: 1). In some embodiments, the N-terminal nucleotide binding domain of TDP-43 comprises SEQ ID NO: 1.

Other nucleic acid molecules that encode TDP-43 within the invention are variants of a native TDP-43, such as those that encode fragments, analogs and derivatives of native TDP-43. Such variants may be, for example, a naturally occurring allelic variant of a native TDP-43 gene, a homolog or ortholog of a native TDP-43, or a non-naturally occurring variant of a native TDP-43 gene. These variants have a nucleotide sequence that differs from a native TDP-43 gene in one or more bases. For example, the nucleotide sequence of such variants can feature a deletion, addition, or substitution of one or more nucleotides of a native TDP-43 gene. Nucleic acid insertions are preferably of about 1 to 10 contiguous nucleotides, and deletions are preferably of about 1 to 10 contiguous nucleotides.

The present invention provides an adenovirus or adenoviral vector that can be used to express a TDP-43 chimeric/fusion protein. The nucleic acids encoding the chimeric protein can be made by preparing a construct (e.g., an expression vector) that expresses a TDP-43 fusion protein when introduced into a suitable target cell. For example, such a construct can be made by ligating a first polynucleotide encoding a TDP-43 protein fused in frame with a second polynucleotide encoding a splicing repressor such that expression of the construct in a suitable expression system yields a fusion protein.

A variant TDP-43 displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue (e.g., serine or threonine), for (or by) a hydrophobic residue (e.g., leucine, isoleucine, phenylalanine, valine or alanine); (b) a cysteine or proline for (or by) any other residue; (c) a residue having an electropositive side chain (e.g., lysine, arginine, or histidine), for (or by) an electronegative residue (e.g., glutamine or aspartine); or (d) a residue having a bulky side chain (e.g., phenylalanine), for (or by) one not having a side chain, (e.g., glycine).

The chimeric TDP-43 protein also includes a splicing repressor. Splicing repressor proteins bind to splicing silencers sites (e.g., cryptic exons) which, reducing the probability that a nearby site will be used as a splice junction. The splicing silencer sites can be located in the intron itself (intronic splicing silencers, ISS) or in a neighboring exon (exonic splicing silencers, ESS). They vary in sequence, as well as in the types of proteins that bind to them. The majority of splicing repressors are heterogeneous nuclear ribonucleoproteins (hnRNPs) such as hnRNPA1 and polypyrimidine tract binding protein (PTB). Examples of splicing repressors include RAVER1, polypyridine tract-binding protein 1 (PTBP1), PTBP2, SRp39, Rbm20, hnRNP A1, and REST.

In some embodiments, the splicing repressor is ribonucleoprotein PTB-binding 1 (RAVER1). RAVER1 is the gene encoding a ribonucleoprotein that is a corepressor of polypyrimidine tract binding protein 1 (PBP1), which is a well-studied splicing repressor. See Ling et al., Cell Reports, 17, 104-113 (2016). An example is human RAVER1 having an NCBI mRNA Reference Sequence NM_133452.2 and an NCBI Protein Reference Sequence NP_597709.2. In further embodiments, the splicing repressor is the minimal repressor domain of RAVER1 consisting of amino acids 450-643 of the NCBI Protein Reference Sequence, which corresponds to the amino acid sequence (SEQ ID NO: 4)
GKPPPLLPSVLGPAGGDREALGLGPPAAQLTPPPAPVGLRGSGLRGLQKD

SGPLPTPPGVSLLGEPPKDYRIPLNPYLNLHSLLPASNLAGKEARGWGGA

GRSRRPAEGPPTNPPAPGGGSSSSKAFQLKSRLLSPLSSARLPPEPGLSD

SYSFDYPSDMGPRRLFSHPREPALGPHGPSRHKMSPPPSGFGER.

The chimeric TDP-43 protein is a protein having an N-terminal domain from the N-terminal nucleotide binding domain of TDP-43 that has TDP-43 binding activity, and a C-terminal domain derived from a splicing repressor that is capable of repressing splicing. An example of a nucleotide sequence encoding such a chimeric protein is one in which the non-native nucleotide sequence comprises SEQ ID NO: 2. SEQ ID NO: 2 is shown below:

ATGTCTGAATATATTCGGGTAACCGAAGATGAGAACGATGAGCCCATTGA

AATACCATCGGAAGACGATGGGACGGTGCTGCTCTCCACGGTTACAGCCC

AGTTTCCAGGGGCGTGTGGGCTTCGCTACAGGAATCCAGTGTCTCAGTGT

ATGAGAGGTGTCCGGCTGGTAGAAGGAATTCTGCATGCCCCAGATGCTGG

CTGGGGAAATCTGGTGTATGTTGTCAACTATCCAAAAGATAACAAAAGAA

AAATGGATGAGACAGATGCTTCATCAGCAGTGAAAGTGAAAAGAGCAGTC

CAGAAAACCAGCGACCTGATTGTCCTGGGTCTCCCATGGAAAACAACCGA

ACAGGACCTGAAAGAGTATTTTAGTACCTTTGGAGAAGTTCTTATGGTGC

AGGTCAAGAAGGACTTGAAGACAGGACATAGCAAGGGGTTTGGCTTTGTT

CGTTTTACGGAATATGAAACACAAGTGAAAGTAATGTCACAGCGACATAT

GATAGATGGACGATGGTGTGACTGCAAACTTCCTAATTCTAAGCAAAGCC

AAGATGAGCCTTTGAGAAGCAGAAAAGTGTTTGTGGGCGCTGTACTGAG

GACATGACTGAGGATGAGCTGCGGGAGTTCTTCTCTCAGTACGGGGATGT

GATGGATGTCTTCATCCCCAAGCCATTCAGGGCCTTTGCCTTTGTTACAT

TTGCAGATGATCAGATTGCGCAGTCTCTTTGTGGAGAGGACTTGATCATT

AAAGGAATCAGCGTTCATATATCCAATGCCGAACCTAAGCACAATAGCAA

TAGAACGCGTGGCAAGCCTCCACCTCTGCTGCCATCCGTGCTTGGACCTG

CTGGAGGTGACAGAGAGGCTCTGGGCTTGGGTCCTCCAGCAGCTCAGCTC

ACTCCTCCACCAGCACCTGTGGGACTCCGAGGCTCTGGCCTCAGAGGCCT

CCAGAAAGACAGTGGGCCTCTGCCGACGCCTCCTGGAGTCTCACTGCTGG

GAGAACCTCCTAAGGACTACCGGATTCCACTGAATCCCTACCTGAACCTA

CACAGCCTGCTCCCTGCCAGCAACCTGGCGGGTAAGGAAGCTAGAGGCTG

GGGAGGCGCCGGAAGAAGCCGCCGCCCAGCTGAGGGCCCTCCAACTAACC

CTCCAGCACCTGGAGGTGGCAGCAGCAGCAGCAAAGCCTTCCAGCTCAAG

TCTCGCCTGCTCAGTCCACTCAGCAGCGCACGCCTGCCTCCTGAACCAGG

ACTGTCTGACAGCTACAGCTTCGACTATCCCTCGGACATGGGACCTAGAC

GGCTCTTCAGCCACCCACGGGAACCAGCCCTTGGGCCTCACGGACCCAGC

CGACACAAGATGTCTCCTCCACCAAGTGGCTTCGGCGAACGGTAG

The non-native nucleotide sequence that expresses the chimeric TDP-43 protein also includes an autoregulatory element. In some embodiments, the autoregulatory element comprises the nucleotide sequence (SEQ ID NO: 3)
tgcccagtctctttgtggagaggatttgatcattaaaggaatcagcgtgc atatatccaatgctgaacctaagcataatagcaatagacagttagaaaga agtggaagatttggtggtaatccaggtggctttgggaatcagggtgggtt tggtaacagtagaggggtggagctggcttgggaaataaccagggtggta atatgggtggagggatgaactttggtgcttttagcattaacccagcgatg atggctgcggctcaggcagcgttgcagagcagttggggtatgatgggcat gttagccagccagcagaaccagtcgggcccatctgggaataaccaaagcc agggcagcatgcagagggaaccaaatcaggcttttggttctggaaataat tcctacagtggttctaattctggtgccc.

Other nucleotide sequence elements which facilitate expression of the TDP-43 gene and cloning of the vector are further contemplated. For example, the presence of enhancers upstream of the promoter or terminators downstream of the coding region, for example, can facilitate expression. Examples of promoters that can be used include: RNA polymerase II promoters such as SV (simian virus) 40 promoter, CMV (cytomegalovirus) promoter, β-actin promoter, EF (elongation factor) 1α promoter, and CAG promoter; and RNA polymerase III promoters such as U6 and H1 promoters.

The nucleotide sequence included in the adenovirus or adenoviral vector can also include a sequence which facilitates the secretion of a TDP-43 gene product from the target cell. The nucleic acid sequence may also contain non-coding 5' and 3' sequences, such as transcribed, non-translated sequences, splicing and polyadenylation signals, ribosome binding sites and sequences that stabilize mRNA.

The adenoviral vector and the non-native nucleotide sequence capable of expressing a TDP-43 chimeric protein can be made recombinantly as set forth in the examples or by other methods of making recombinant viruses as described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Similar methods are used to introduce a gene of interest in methods of making the viral vector described herein. For example, recombinant viruses can be constructed using homologous recombination after DNA co-transfection. In this example, cells can be co-transfected with at least two different viruses containing the genes of interest and progeny virus plaque can be purified based upon loss of marker expression. Final verification of the correct genetic organization of candidate viruses can be verified by DNA hybridization studies using probes to the nucleic acids as described herein.

The TDP-43 chimeric protein is included in an adenovirus or adenoviral vector. The adenovirus has yielded results in clinical trials on the gene therapy of Parkinson's disease, Alzheimer's disease, etc. In addition, the adenovirus has been reported to express a gene or a microRNA in a neural-specific manner in mouse models of various neurodegenerative diseases and thereby exert therapeutic effects (see Japanese Patent No. 4279141). Thus, the adenovirus can be particularly preferably used in the present invention. For example, a composition including adeno-associated virus encoding ADAR2 gene under the control of a neural-specific promoter (synapsis gene promoter) was intravenously injected to ALS mouse models so that the gene was specifically expressed in neurons, producing therapeutic effects (Yamashita T., et al., EMBO Mol. Med., 5: 1710-1719, 2013). These techniques may be applied to the present invention.

Adenoviruses are generally associated with benign pathologies in humans, and the genomes of adenoviruses isolated from a variety of species, including humans, have been extensively studied. Adenovirus is a medium-sized (90-100 nm), nonenveloped icosahedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., Virology, 28: 782-83 (1966)). The hexon comprises three identical proteins, namely polypeptide II (Roberts et al., Science, 232: 1148-51 (1986)). The penton base comprises five identical proteins and the fiber comprises three identical proteins. Proteins Ma, VI, and IX are present in the adenoviral coat and are believed to stabilize the viral capsid (Stewart et al., Cell, 67: 145-54 (1991), and Stewart et al., EMBO J., 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"). For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., Hum. Gene Ther., 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

Both human and non-human adenoviral vectors can be used and the recombinant viral vector can be replication-defective in humans Where the vector is an adenovirus, the vector can comprise a polynucleotide having a promoter operably linked to a gene encoding the TDP-43 and is replication-defective in humans. The adenovirus and adenoviral vector can be replication-competent, conditionally replication-competent, or replication-deficient.

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

In some embodiments, the adenovirus or adenoviral vector is a particular adenovirus serotype. Examples of adeno-associated virus serotypes include AAV1, AAV2, AAV4. AAV5. AAV6, AAV7, AAV8, and AAV9, and AAVPhP.eB. AAvPhP.eB is a variant adeno-associated virus particle named after the researcher Paul H. Patterson that has been modified to increase its ability to cross the blood-brain barrier. In some embodiments, the adenovirus or adenoviral vector used is AAV0 or AAVPhP.eB.

Treatment of Disease Manifesting TDP-43 Dysfunction or Dysregulation

Another aspect of the present invention provides a method for treating a subject having a disease manifesting transactivation response element DNA-binding protein 43 (TDP-43) dysfunction or dysregulation, comprising administering a therapeutically effective amount of a nucleotide sequence capable of expressing a chimeric protein comprising an N-terminal nucleotide binding domain of TDP-43 and a C-terminal domain derived from a splicing repressor using an adenovirus or adenovirus vector.

Any of the embodiments of the chimeric TDP-43 protein and the adenovirus vector described herein can be used for treating a subject. For example, in some embodiments, the splicing repressor is ribonucleoprotein PTB-binding 1 (RAVER1). In other embodiments, the adenovirus is AAV9 or AAVPhP.eB. In further embodiments, the N-terminal nucleotide binding domain of TDP-43 comprises SEQ ID NO: 1.

TDP-43 aggregation and neuropathology plays a fundamental role in a broad spectrum of neurodegenerative disorders. See, e.g., Cohen et al., 2011, Trends Mol. Med. 17, 659-667. Cytosolic accumulation of truncated TDP-43 is found in affected neurons of patients suffering from sporadic and familial ALS and FTLD. Missense mutations clustering in the TDP-43 GRD have been identified in cases of ALS (and FTLD). See, e.g., Hancks and Kazazian, 2012, 22, 191-202.

Elevated levels of the TDP-43 protein have also been identified in individuals diagnosed with chronic traumatic encephalopathy, a condition that often mimics ALS and that has been associated with athletes who have experienced multiple concussions and other types of head injury. See, e.g., Baugh et al, 2012, Brain Imaging Behav. 6, 244-254. TDP-43 pathology has also been implicated in tauopathies other than AD, such as corticobasal degeneration, as well as in Lewy body related disorders, including Parkinson's disease (PD) without or with dementia (PDD), and dementia with LBs (DLB) alone or in association with Alzheimer disease (AD). See, e.g., Uryu et al., 2008, J. Neuropathol. Exp. Neurol. 67, 555-564.

In the present specification, a "disease manifesting TDP-43 dysfunction or dysregulation" refers to a disease involving structural abnormality and intracellular localization abnormality of the TDP-43 protein compared to that in healthy individuals. The abundance of TDP-43 per cell is extremely strictly controlled in cells of healthy individuals (Ayala, Y. M., et al., 2011, EMBO J. 30 (2) 277-288). The disease manifesting TDP-43 dysfunction or dysregulation may be any type of disease in which the intracellular localization of TDP-43 in cells varies beyond a normal range.

In one aspect, the disease is a degenerative disease or disorder, particularly a neurodegenerative disorder. In another aspect, the neurodegenerative disorder is a TDP-43 associated neurodegenerative disorder. Inclusion body myositis (IBM) is an example of a degenerative disease involving TDP-43 dysfunction or dysregulation. Neurodegenerative disorders within the scope of this invention include frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body disorder (such as Parkinson disease without or with dementia (PDD), and dementia with LBs (DLB) alone or in association with Alzheimer disease (AD)).

The adenovirus or adenoviral vector used for expressing the chimeric TDP-43 protein can be preferably administered as a prophylactic or therapeutic drug to a subject manifesting a TDP-43 dysfunction or dysregulation or suspected of having the disease. In some embodiments, the disease manifesting TDP-43 dysfunction or dysregulation is amyotrophic lateral sclerosis or frontotemporal dementia. In other embodiments, the disease manifesting TDP-43 dysfunction or dysregulation is inclusion body myocytosis.

Protecting Motor Neurons

Another aspect of the invention provides a method of protecting motor neurons having transactivation response element DNA-binding protein 43 (TDP-43) dysfunction or dysregulation. The method includes contacting the motor neurons with an effective amount of a chimeric protein comprising an N-terminal nucleotide binding domain of TDP-43 and a C-terminal domain derived from a splicing repressor. Contacting the motor neuron involves putting the chimeric TDP-43 protein in proximity to the motor neuron so that the chimeric TDP-43 protein will interact with the motor neuron. The inventors have shown herein that TDP-43 mediated splicing repression is central to motor neuron physiology, and therefore a chimeric TDP-43 protein as described herein can be used to protect motor neurons from TDP-43-mediated dysfunction. The motor neuron can be contacted either in vivo, ex vivo, or in vitro.

Motor neurons are neurons located in the motor cortex, brainstem, or spinal cord whose axon protects to the spinal court or outside of the spinal cord to directly or indirectly control effect organs, and in particular muscles and glands. Motor neurons typically express the marker genes HB9 and ChAT (choline acetyltransferase). Motor neurons play an important role in many diseases involving motor dysfunction, such as ALS.

Methods of Diagnosing IBM

Another aspect of the invention provides a method for diagnosing inclusion body myositis (IBM) in a subject. The method includes the steps of: contacting a biological sample from a subject with one or more nucleic acid probes specific for a cryptic exon associated with IBM, determining if one or more of the nucleic acid probes have associated with a cryptic exon associated with IBM, and characterizing the subject as having an increased risk for IBM if association of a nucleic acid probe with a cryptic exon associated with IBM is detected. The method can further include the step of treating the subject diagnosed as having IBM by administering a therapeutically effective amount of a chimeric TDP-43 protein to the subject using an adenovirus or adenoviral vector.

The method for detecting the presence of cryptic exons associated with IBM include any method known in the art for detecting nucleotide sequences. For example, a detection method using a nucleic acid probe which has a nucleotide sequence complementary to all or part of the nucleotide sequence of the target cryptic exon, and is capable of specifically hybridizing to and detecting the target cryptic exon, or quantitative RT-PCR may be used. Examples of detection methods using a nucleic acid probe include Northern blotting, surface plasmon resonance (SPR) or quartz crystal microbalance (QCM). All the methods mentioned above are techniques known in the art and may be performed in the present invention according to a known procedure. Specifically, reference may be made to the methods described, for example in Sambrook, J. et al. (2001) Molecular Cloning: A Laboratory Manual Third Ed., Cold Spring Harbor Laboratory Press, Cold Spring Harbor, N.Y., and Toyosaka Moriizumi, Takamichi Nakamoto (1997), Sensor Engineering, Shokodo, Co., Ltd., Toshifumi Inada, Haruhiko Shiomi, 2008, Yodosha Co., Ltd., Notebook for RNA Experiment (1997). Two or more of the methods described above may be used in combination to obtain more accurate measurement results.

Preferably the nucleic acid probe is labeled so that it can be more easily detected. a "labeled nucleic acid probe" is a nucleic acid that is bound, either covalently, through a linker or a chemical bond, or noncovalently, through ionic, van der Waals, electrostatic, or hydrogen bonds to a label such that the presence of the labeled protein or nucleic acid may be detected by detecting the presence of the label bound to the labeled protein or nucleic acid. Alternatively, methods using high affinity interactions may achieve the same results where one of a pair of binding partners binds to the other, e.g., biotin, streptavidin.

In some embodiments, the cryptic exons associated with IBM are present in a gene selected from the group consisting of RANBP1, ADAMT56, ZC3H12C, PPP2R2D, ZNF529, USP13, BIRC3, CD01, FAM114A2, ACSF2, CEP72, PKN1, GPSM2, 5LC39A8, XP04, ST5, ACOT11, SLC17A9, PFKP, HDGFRP2, BCL2L13, ZFP91, and RHEBL1.

The genes in which the cryptic exon associated with IBM are present include a nucleotide sequence that can be used as a target for a nucleic acid probe. The nucleic acid sequences are the cryptic exons of various sequences are shown below in Table 1:

TABLE 1

Cryptic Exon Sequences Associated with IBM

| | |
|---|---|
| RANBP1 | ACGUGCCUCUGAACUCAGAGCAGGCGCCCAGGCUGGGC UCGGGACGAGGA (SEQ ID NO: 5) |
| ADAMT56 | GGGUCCCCAACCAUGGCCUGUUAGGCCGCACAGUGGGA AGUCAGCUGCAG (SEQ ID NO: 6) |
| ZC3H12C | CUUAGUAAAUGGUUGUAAUGUGGUAAACUGCUGAUAUU GCUUCAACUAAG (SEQ ID NO: 7) |

TABLE 1-continued

Cryptic Exon Sequences Associated with IBM

| Gene | Sequence |
|---|---|
| PPP2R2D | CGUGGGGUAUGUGUGCAGCAUUUCAUAAAUUUUAAAU GUUUAACUGGAU (SEQ ID NO: 8) |
| ZNF529 | GUUAGUGCUAUUGUUUACGACGUCAGUGCUGUUUGAUC GGACUCAGGACG (SEQ ID NO: 9) |
| USP13 | GUCAGUGAGUGUGCACGGCUGCUAGCUAGAUGCGCAUG GCUCUGUGUCAG (SEQ ID NO: 10) |
| BIRC3 | UGUUGCCUAAAUUUCCACAAAUAUGUCUCCUGAGUAGC UGGAAAUACAG (SEQ ID NO: 11) |
| CD01 | UCGUGGUCGUGGUUUGCAGUUUGUUGUGGCAGUGGUGG UGGUUGGUUGUG (SEQ ID NO: 12) |
| FAM114A2 | GUACUGUGGUACUACUUGGUACGUAUACUUCUUAGUUG GUUUGUAUGUCA (SEQ ID NO: 13) |
| ACSF2 | GCCAUGUGUGAUUGGAAGGUGGCCCGUGGUUGGUCAGA CACAAACCUGGC (SEQ ID NO: 14) |
| CEP72 | GCCCUUCAUGCUGUCUGUCGCAUGUAUGGACUGUGAGA UGGGACUGUGAG (SEQ ID NO: 15) |
| PKN1 | GACUGGCCCUGUGAGUGAUGGUGUUACUGCCCUGUAUU CCACGCUCACAG (SEQ ID NO: 16) |
| GPSM2 | GGUAGAGAGUGAGUGUGUGUUGUGUGUGUAUGAGAGAG AGAGCGAACAG (SEQ ID NO: 17) |
| 5LC39A8 | GCACUCCAUUCUUAUUGCUGUGUGUGUGGUGAAAGAGA GAGAGAGAUUAG (SEQ ID NO: 18) |
| XP04 | GUUAGCCCAUUGUUGGAGGCUGACUGCUGACUGUGUGU GUAUGUGUGUGG (SEQ ID NO: 19) |
| ST5 | AGUGGAAGCUCCUUGAGGAUGGACCAUAUUAGCUGAAU GGAUGCAUGACU (SEQ ID NO: 20) |
| ACOT11 | GGCCGGACACACACAAGAGGUGGUCUGCUGGAAGAACU GCAGGAGUGUAU (SEQ ID NO: 21) |
| SLC17A9 | GUAAGGGGAGCUCAGGCGGCUCCCUUCUAGAGCACAGC UGGAGGCCGGUG (SEQ ID NO: 22) |
| PFKP | AAAUAAUCCAAAUCGGUGCCUCCCCGAUAAGAUGUGAA CGGAGAGUUGAA (SEQ ID NO: 23) |
| HDGFRP2 | GAGCCCACCAUCUGGUUUGGAAAGGGAGGGACACAGAA GAGAGGAGAGAG (SEQ ID NO: 24) |
| BCL2L13 | GCUGGACUACAGUGGCACGAUCAUAUCCUGAGUUGAGU AGAUGAGACUAC (SEQ ID NO: 25) |
| ZFP91 | GCAAACAGAAGAAGAUCAGAUUAGUAACAUUUCCCAAU CCUCCAAAAGAA (SEQ ID NO: 26) |
| RHEBL1 | GUGAGUCUCCGCCCUGCAGAGCUCGGCGAGGAUUGGAA GAGUGGAGGAAU (SEQ ID NO: 27) |

As used herein, the term "biological sample" means sample material derived from or contacted by living cells. The term "biological sample" is intended to include tissues, cells and biological fluids isolated from a subject, as well as tissues, cells and fluids present within a subject. Biological samples include, e.g., but are not limited to, whole blood, plasma, serum, semen, cell lysates, saliva, tears, urine, fecal material, sweat, buccal, skin, synovial fluid, cerebrospinal fluid, and hair. Biological samples can also be obtained from biopsies of internal organs. Preferably, the biological sample for a muscle degenerative disease is muscle tissue, sample, while the preferred biological sample for neurodegenerative diseases is cerebrospinal fluid sample.

The method can also include the step of the step of obtaining a biological sample from a subject. Alternately, in some embodiments, the biological samples may have already been obtained. Biological samples can be obtained from subjects for diagnosis prognosis, monitoring, or a combination thereof, or for research, or can be obtained from un-diseased individuals, as controls or for basic research. Biological samples can be obtained by any known means including needle stick, needle biopsy, swab, and the like.

A biological sample may be fresh or stored. Samples can be stored for varying amounts of time, such as being stored for an hour, a day, a week, a month, or more than a month. The biological sample may be a bodily fluid expressly obtained for the method of the invention or a bodily fluid obtained for another purpose which can be sub-sampled for the methods of the invention.

Formulations and Methods of Administration

The TDP-43-containing adenovirus and adenoviral vectors described herein can be administered in vitro or in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). These may be targeted to a particular cell type via antibodies, receptors, or receptor ligands. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Pharmaceutical compositions may include carriers, thickeners, diluents, buffers, preservatives, surface active agents and the like in addition to the molecule, in this case virus or viral vector, of choice. Pharmaceutical carriers are known to those skilled in the art. These most typically would be standard carriers for administration of drugs to humans, including solutions such as sterile water, saline, and buffered solutions at physiological pH. Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic.

Examples of a pharmaceutically-acceptable carriers include, but are not limited to, saline, Ringer's solution and dextrose solution. The pH of the solution is preferably from about 5 to about 8, and more preferably from about 7 to about 7.5. Further carriers may include sustained release preparations such as semipermeable matrices of solid hydrophobic polymers containing the antibody, which matrices are in the form of shaped articles, e.g., films, liposomes or microparticles. It will be apparent to those skilled in the art that certain carriers may be more preferable depending upon, for instance, the route of administration and concentration of composition being administered.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as; for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The TDP-43-containing adenovirus and adenoviral vectors can be administered in a number of ways depending on whether local or systemic treatment is desired, and on the area to be treated. Administration may be topical, oral, by inhalation, or parenterally, for example by intravenous drip, subcutaneous, intraperitoneal or intramuscular injection. The disclosed viruses and vectors can be administered intravenously, intraperitoneally, intramuscularly, subcutaneously, intracavity, or transdermally. Thus, administration of the provided viruses and vectors to the brain can be intracranial, subdural, epidural, or intra-cisternal. For example, the provided viruses and vectors can be administered directly into the tumors by stereotactic delivery. It is also understood that delivery to tumors of the CNS can be by intravascular delivery if the virus or vector is combined with a moiety that allows for crossing of the blood brain barrier and survival in the blood. Thus, agents can be combined that increase the permeability of the blood brain barrier. Agents include, for example, elastase and lipopolysaccharides. The provided viruses and vectors are administered via the carotid artery. In another aspect, the provided viruses and vectors are administered in liposomes, such as those known in the art or described herein. The provided viruses and vectors can be administered to cancers not in the brain intravascularly or by direct injection into the tumor.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein for the methods taught therein.

It is also possible to link molecules (conjugates) to viruses or viral vectors to enhance, for example, cellular uptake. Conjugates can be chemically linked to the virus or viral vector. Such conjugates include but are not limited to lipid moieties such as a cholesterol moiety. (Letsinger et al., Proc. Natl. Acad. Sci. USA, 1989, 86:6553-6556).

The viruses and viral vectors described herein may be administered, for example, by convection enhanced delivery, which has been used with adenovirus and AAV to increase the distribution of the virus thorough bulk flow in the tumor interstitium. Chen et al., J. Neurosurg. 103(2): 311-319 (2005) Genetic modifications have also been used to enhance viral spread. For example, insertion of the fusogenic glycoprotein gene produced an oncolytic virus with enhanced antiglioma effect. Fu et al., Mol. Ther. 7(6): 748-54 (2003). Therefore, the TDP-43-containing adenovirus and adenoviral vectors described herein may comprise such a gene.

Dosages

The exact amount of TDP-43-containing adenovirus or adenoviral vectors required will vary from subject to subject, depending on the species, age, weight and general condition of the subject, the severity of the disease being treated, the particular virus or vector used, its mode of administration and the like. Thus, it is not possible to specify an exact amount for every application. However, an appropriate amount can be determined by one of ordinary skill in the art using only routine experimentation given the teachings herein.

The dosage ranges for the administration of the compositions are those large enough to produce the desired effect in which the symptoms of the disease are affected. The dosage should not be so large as to cause adverse side effects, such as unwanted cross-reactions, anaphylactic reactions, and the like. The dosage can be adjusted by the individual physician in the event of any counterindications. Dosage can vary, and can be administered in one or more dose administrations daily, for one or several days.

Viral recovery and immunohistochemistry have been used successfully to monitor viral replication and spread in vivo. Bioluminescent and fluorescent protein expression by the virus can also be used to indirectly monitor viral replication and spread in the tumor. Genes encoding fluorescent reporter proteins (d2EGFP and dsRED monomer) or bioluminescent markers (firefly luciferase) are commonly used in recombinant viruses. Not only do these facilitate the screening and selection of recombinant viruses in vitro. The reporter genes also allow indirect monitoring of viral activity in in vivo studies.

Examples have been included to more clearly describe particular embodiments of the invention. However, there are a wide variety of other embodiments within the scope of the present invention, which should not be limited to the particular examples provided herein.

EXAMPLES

Example 1: Target Validation of Splicing Repression, a Major Function of TDP-43 in the Motor Neuron Using multiple model systems and an AAV9-mediated gene delivery approach (K. D. Foust et al., Nat. Biotechnol.

28, 271 (2010)), we establish here that TDP-43-mediated splicing repression is central to the physiology of motor neurons.

Materials and Methods

Fly Stocks and Transgenic Flies

Flies were maintained at 25° C. on a standard cornmeal/agar medium. TBPH null mutant TBPHΔ23 was kindly provided by Dr. Fabian Feiguin. All Gal4 driver lines were obtained from the Bloomington Stock Center at Indiana University (Bloomington, IN).

To construct the fly CTR expression vector, a DNA fragment corresponding to aa1-267 of human TDP-43 and aa450-643 of RAVER1 was subcloned into pUAST from CTR vector using the following primers: Forward primer CCGCTCGAGACCATGGCCTCTGAATATATTCG (XhoI NTDP-F); Reverse primer: CGTCTAGAC-TACCGTTCGCCGAAGCCACTTG (XbaI CRAV-R). For the NTDP construct, the following primers were used: forward primer, ATCTCGAGATGGT-GAGCAAGGGCGAGGA (XhoI-GFP-F); Reverse primer: ATCTAGACTATCTATTGCTATTGTGCTTAGGTTCGGC (XbaI-NTDP-R). All transgenic fly strains were generated by BestGene.

Library Construction and Massively Parallel Sequencing

RNA was extracted from fly heads using TRIzol. Total RNA for RNA-seq was then processed using the TruSeq Stranded Total RNA Library Prep Kit (Illumina) to construct 100-bp paired end stranded RNA-seq libraries. Sample libraries were sequenced on a HiSeq 2000 to generate approximately 70 million reads per sample which was de-multiplexed and converted into fastq files. Fastq files were aligned to *Drosophila* genomes using TopHat and annotated using Cufflinks on Galaxy, an open-source, web-based bioinformatics platform. Cryptic exons were initially identified through manual screening of novel exons annotated by Cufflinks that were highly abundant in the Tdp-43 knockout dataset but not control. TopHat aligned data was then displayed to the UCSC Genome Browser to visualize RNA-seq coverage.

RNA Analysis (*Drosophila*)

Total RNA from fly heads was purified using RNeasy mini kit (Qiagen) according to manufacturer's instructions. The cDNA synthesis was performed starting from 1ug of each RNA sample using RevertAid RT reverse transcription Kit (Thermo Scientific). PCR analysis for cryptic exons has been performed using the following primers: Rugose-F TGTTGCATGTGTGAGCGTGG; Rugose-R GCTGTTG-GAGCGTTTGATGT. Pkc53E-F TTCGAGCCATTCACAT-ACGC; PKC53E-R TTCCCACGCAGACACTCACA; Sev-F AGTTCTGCTGCGATCGCGCC; Sev-R CAGCAACAACAACAGCACAG; Pyd-F CTA-GATCCTCAGTCCGTTAAC; Pyd-R CTGATCGATAT-CATTGCCAAGA. CG42450-F TGTGTGTGTTTGTGG-GAGTGTG; CG42450-R GTGTCAGGACCTTAAAGGCGGT; Uif-F GCGCGTTGTGGACGTTAAGA; Uif-R GCCGTACT-GAAGAAAACCCA; Dyb-F1 CGCGA-TAAGTGCAGAGAAACAG; Dyb-R1 GCTATGGATGG-GAATTCCGCAT; CG8045-F1 GGTGTGTGTGTGTGTGTGTGTGTGCAC; CG8045-R ACCTGGTGCTGGGCCATGAT.

Video-Assisted Movement Tracking

Tracking arenas were 3.5 cm diameter Petri dish (Corning) filled with transparent silicon elastomer (Dow Corning) with a 3-mm space so that flies could walk freely but not fly. A CCD camera positioned above the arenas was connected to a PC. Three flies were briefly anaesthetized with $CO_2$, placed in the arena and left to recover at 22° C. for 1 hour before being tested. Tracking was carried out at 22° C. Recorded videos were converted to fly movie format using the motmot package and loaded into Ctrax software to analyze the positions of the flies throughout the video. Position data for the 5-min file was exported as a matrix file. Errors in the tracking were fixed using Matlab (Mathworks) as well as FixErrors GUI. Fixed trajectories were analyzed in Matlab to calculate the mean cumulative distance travelled by the population of flies in the arena. Significance was calculated using the Mann-Whitney U-test with a Bonferroni correction to account for multiple comparisons.

Lifespan Analysis

Flies were maintained on standard medium at 25° C. Each group of flies was aged in individual vials containing no more than 20 flies and were transferred to a new vial every 1-2 days. The number of dead flies was recorded for longevity analysis.

Mouse Generation

All mouse procedures were performed in accordance with the National Institutes of Health Guide for the Care and Use of Laboratory Animals and were approved by the Johns Hopkins University Animal Care and Use Committee.

We crossbred our previously described conditional Tardbp knockout mice (TardbpF/F, Jax stock 017591) with ChAT-IRES-Cre transgenic mice on a C57BL/6J background (Jax stock 006410) to obtain a cohort of ChAT-IRES-Cre;Tardbp$^{F/+}$ mice. These were subsequently crossed again with Tardbp$^{F/F}$ mice to generate the final cohort of ChAT-IRES-Cre;Tardbp$^{F/+}$ (control) and ChAT-IRES Cre;Tardbp$^{F/F}$ (Tdp-43 knockout) mice. All mice were housed under a 12 L:12 D daily cycle and managed by Johns Hopkins University Research Animal Resources (RAR).

Viral Vector Packaging

AAV9 packaging was performed by Virovek (Hayward CA), and CTR or GFP expression was independently confirmed by HeLa cell transduction and western blot prior to all experiments.

Intracerebroventricular (ICV) Injection

All injections were performed on mouse pups within 8 hours of birth. Pups were cryo-anaesthetized on wet ice for no longer than 2 minutes. A latex barrier between pups and ice prevented skin damage. A sterile, single-use pulled glass needle (Drummond microcaps, 41 mm length, approx. 0.5 mm minimum diameter) was penetrated 3 mm into the lateral ventricle of each cryo-anaesthetized mouse pup to slowly deliver 3 μl of AAV9 ($1E10^{13}$ vg/ml) carrying either our chimeric splicing repressor protein, termed CTR, or GFP into the lateral ventricles over 15 seconds; solutions contained 0.05% trypan blue dye for localization. Pups recovered under a heat lamp with bedding from their home cage in order to restore scent, after which they were returned to their mother cage and monitored after 6 and 12 hours and daily afterwards. A successful injection was identified by dye-induced darkening of the spinal column at 6 hours post-injection. Approximately 80% of pups successfully recovered from injection, with 10% insufficiently recovering from anesthesia at p0-p1 and 10% displaying signs of hydrocephaly at p14-p21. All pups showing signs of distress at any time following recovery were euthanized.

Sample Size

All litters were injected prior to genotyping. For motor function and survival analyses, a total of 40 mice from 8 litters were injected for cohort 1. Every pup in each litter was injected at random with an AAV9 vector carrying either our CTR fusion protein or GFP as a control, and all pups in each litter received either CTR or GFP. A total of 8 ChAT-IRES-Cre;Tardbp$^{F/+}$ mice were injected with GFP, 8 ChAT-IRES-Cre;Tardbp$^{F/+}$ mice were injected with CTR, 11 ChAT-IRES-Cre;Tardbp$^{F/F}$ were injected with GFP, and 11 ChAT-IRES-Cre;Tardbp$^{F/F}$ mice were injected with CTR. The size of cohort 1 was sufficiently powered to measure a mean survival increase of 50% with 25% standard deviation ($1-\beta=0.994$). We then replicated our results by injecting a second cohort of mice from the same breeder pairs, termed 'cohort 2'. Each litter in cohort 2 received the opposite payload as its cohort 1 counterpart. Four additional cohorts, each from the same breeder pairs, were bred and injected for analysis of spinal cord pathology at 1 month, 3 months, and 5 months (pathology analysis cohorts) and for injection of an AAV9 vector carrying only the N-terminal fragment (NTF) of TDP-43 as another control (NTF cohort).

Hanging Wire Test

Hanging wire tests were performed weekly beginning at p30. Investigators were blinded to the treatment group of each animal. Each mouse was placed on the center of a metal grid that then was shaken gently to prompt the mouse to hold on before being turned upside down 30 cm over an empty cage. Each mouse was allowed up to three attempts to hold on to the inverted grid for an arbitrary maximum of 60 seconds. Mice were given >2 minutes of rest between attempts, and the best attempt was used for analyses.

Accelerating Rotarod Test

Rotarod tests were performed once every two weeks with an initial acclimatization session beginning at p30. Investigators were blinded to the treatment group of each animal. Mice were placed on the apparatus (Rotamex, Columbus Instruments) with a rod diameter of 3 cm, minimum speed of 4 rpm, and accelerating at 20 rpm/min. Latency to fall was recorded. Each mouse was given three attempts with >30 minutes of rest between attempts, and the best attempt was used for analyses.

Survival

Upon showing symptoms of hindlimb paralysis, mice were provided wet chow and Dietgel on the cage floor. End-stage was defined as a failure of a mouse to right itself within 10 seconds when placed on its back on the cage floor and was tested daily after hindlimb paralysis was observed. Investigators were blinded to the treatment group of each animal. All mice were sacrificed and processed for biochemical and pathological analysis upon reaching end-stage.

RNA Analysis (Mouse)

Whole spinal cords of p45 ChAT-IRES-Cre;Tardbp$^{F/+}$ and ChAT-IRES-Cre;Tardbp$^{F/F}$ mice were dissected, titurated using a 1 mL syringe with a 20-gauge needle, and placed in TRIzol. Total poly-A-containing messenger RNA was extracted using a RNeasy Mini kit (Qiagen) protocol under RNAse-free conditions and converted to cDNA using the Protoscript II First Strand cDNA Synthesis Kit (NEB). Quantitative PCR for cryptic exon mRNA was performed using the PowerUp SYBR Green protocol (Applied Biosystems) with the following primers: GGCT F: GAGGGGTGTTGGAAGGCTGT; GGCT R: TACCACTCCCCACACTTCGT; SYNJ2BP F: CTCCAACGACAGTGGCATCT; SYNJ2BP R: TCTTCCTGAGGACCTCCGTT; IFT81 F: AAGTGCGAGGACTTCGTGAG; IFT81 R: CAGCGATCTGTCTGCTTTGC; GAPDH F: AGGTCGGTGTGAACGGATTTG; GAPDH R: GGGGTCGTTGATGGCAACA; TBP F: AAGGGAGAATCATGGACCAG; TBP R: CCGTAAGGCATCATTGGACT. Each reaction was performed in duplicate, and each RT-PCR experiment independently repeated three times. Relative transcript levels were calculated in Microsoft Excel according to the formula: (POWER(2,−(Ct mean cryptic exon target)))/(POWER(2,−(AVERAGE(Ct mean TBP, Ct mean GAPDH))).

Histological and Immunohistochemical Analysis

All mice from the pathology analysis cohorts were anaesthetized and perfused with 4% paraformaldehyde. The cervical (C5-C8) and lumbar (L1-L3) enlargements and their corresponding spinal ganglions from each mouse were dissected and post-fixed for 24 hours. Spinal ganglions were embedded in epoxy resin and sagittally sectioned at 1 μm thickness. Spinal cords were embedded in paraffin and sagittally sectioned at 10 μm thickness. Sections were stained with hematoxylin/eosin or Cresyl violet for histological analysis.

For immunohistochemical analysis, sections were deparaffinized and incubated in 10 mM citric acid at 95° C. for 10 minutes followed by a 30-minute incubation in 0.3% hydrogen peroxide in methanol to quench endogenous peroxidase activity. Normal goat serum (5%) in PBS-T was used to block nonspecific binding, after which primary antibody in blocking buffer was applied to each section overnight at 4° C. in a humid chamber. Secondary antibodies were applied at room temperature for 2 hours. A Vectastain Universal Elite ABC kit (Vector Laboratories) was used to amplify signal.

Sections were stained with the following primary antibodies: Human-specific N-terminus TDP-43 (hTDP43, 1:500; AB57105, Abcam), Choline acetyltransferase (ChAT, 1:1000; AB144, Millipore), C-terminus TDP-43 (1:500; 12892-1AP, Proteintech), microtubule-associated protein 2 (Map2, 1:1,000; AB5622, Millipore), phosphorylated neurofilament (Smi31, 1:1,000; BioLegend), synaptophysin (1; 1000; SY38/ab8049, Abcam), ionized calcium-binding adapter molecule 1 (IBA1, 1:500; 10904-1AP, Proteintech), glial fibrillary acidic protein (GFAP, 1:500; AB7260, Abcam), phosphorylated tau (Tau422, 1:1000; AB79415, Abcam).

Immunoblot Analysis

Whole spinal cords from mice were flushed and homogenized using a 1 mL syringe with a 20-gauge needle in cold RIPA buffer with protease inhibitor cocktail (Roche). Protein concentration in the supernatants was determined via BCA assay (Pierce), and 10 μg protein was loaded on a 10% Bis-Tris SDS-PAGE gel (Novex) and transferred to a PVDF membrane, which was probed with the following antibodies: N-terminal TDP-43 (1:2000; 10782-2-AP, Proteintech), β-tubulin III (1:20,000; T2200, Sigma).

Statistics

Histological data was analyzed using the unpaired, two-tailed Student's t-test with Tukey's multiple comparison where appropriate, and one-way analysis of variance (ANOVA) test using Stata 10 for Mac (Statacorp) and Graphpad Prism for Mac (Graphpad Software). RNA data was analyzed using the Mann-Whitney test. Error bars represent standard deviation unless otherwise mentioned. Mouse hanging wire, rotarod, and weights were analyzed using two-way ANOVA with Tukey's multiple comparison. Kaplan-Meier survival curves were analyzed using the log-rank test. P values of <0.05 were considered significant.

Splicing Repression as a Major Function of TDP-43 in the Motor Neuron

Figure 2C:
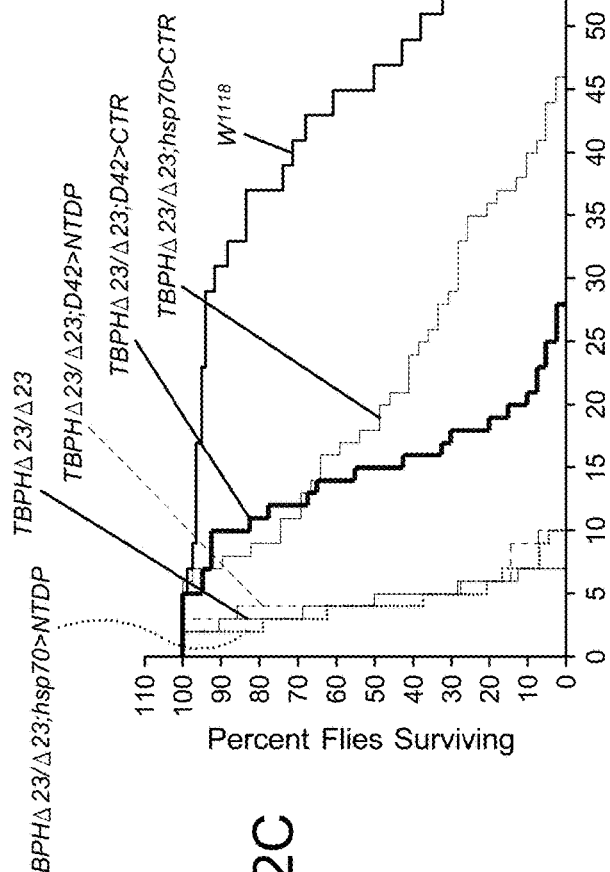
Figure 6A:
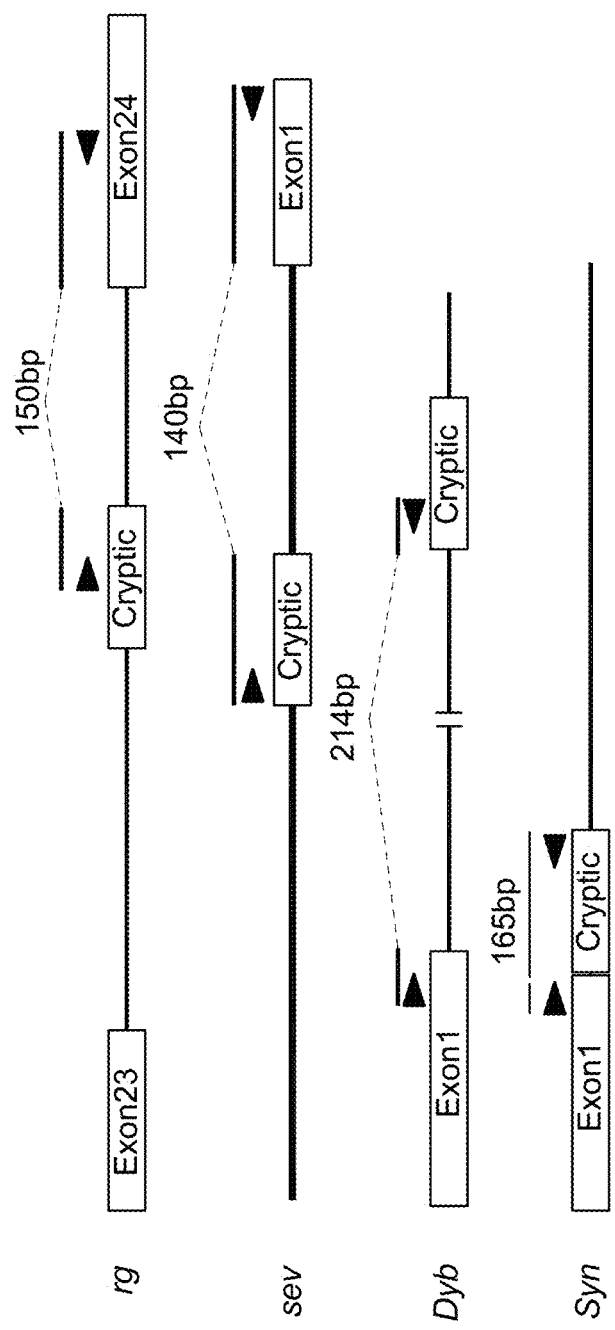
FIGS. 6A-6C provide images showing Sequencing validation of cryptic exon RT-PCR. (A) Diagram of RT-PCR detection strategy. Primers were designed to amplify only the cryptic exon splice junction. (B) Gel purification and sequencing of these RT-PCR bands confirms that these DNA products precisely correspond to the predicted cryptic exon splice junctions. (C) To visualize this, sequencing data was aligned to the *Drosophila* genome using UCSC BLAT; thick bands in the sequence alignment indicate DNA sequences that are present in the RT-PCR product, thin bands represent sequences that have been spliced out. Sequence alignment demonstrates clear overlap with cryptic exon and completely matches the predicted the splice junctions.
Figure 6B:
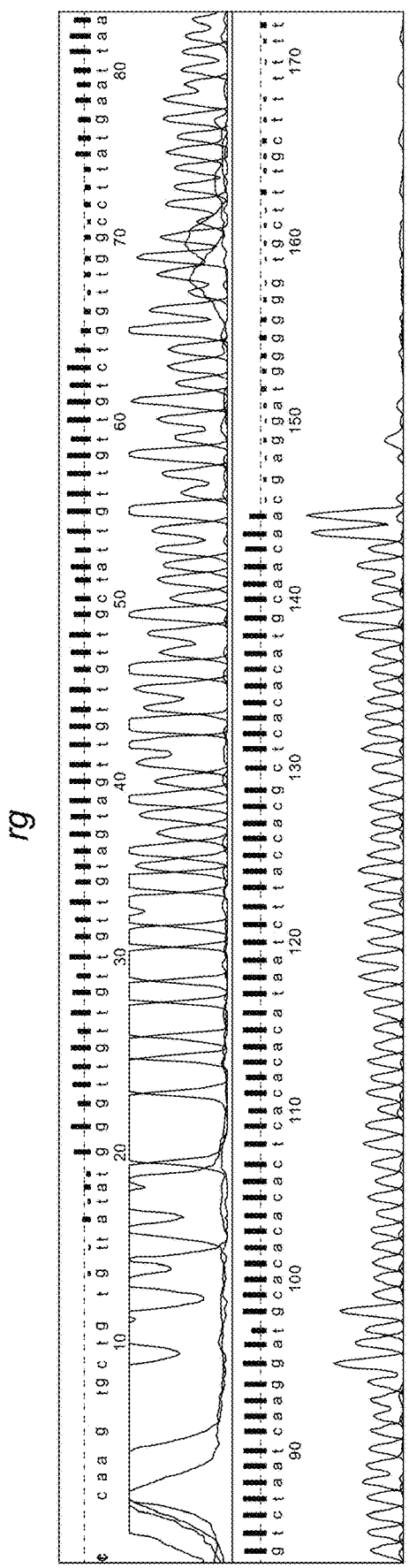
Figure 6C:
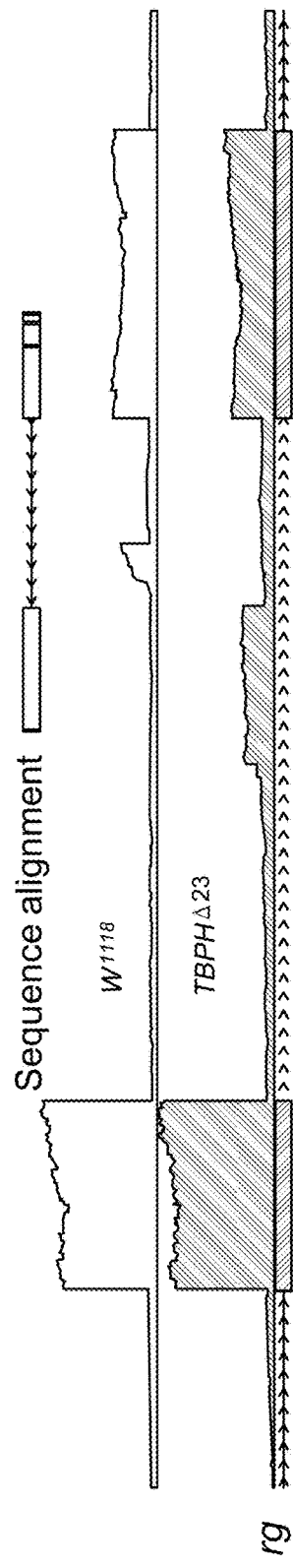

We previously showed that TDP-43 mediated splicing repression can be restored using a chimeric protein, termed CTR, consisting of the RNA-recognizing N-terminal domain of TDP-43 fused with an unrelated, structurally distinct but well characterized splicing repressor, RAVER1. A. P. Rideau et al., Nature Structural and Molecular Biology, 13, 839 (2006). In contrast to replicating cells, it is not known whether splicing repression is a major function of TDP-43 in post mitotic cells, including motor neurons. We took a genetic approach to test whether this chimeric TDP-43 repressor could complement loss of TDP-43 function in motor neurons. We first assessed the ability of CTR to rescue motor phenotype and lethality occurring in a *Drosophila* model lacking TBPH (the fruit fly homolog of TDP-43). F. Feiguin et al., FEBS Lett. 583, 1586 (2009). Flies globally lacking TBPH mostly failed to eclose, and the few surviving adults exhibited impaired locomotion and early lethality along with cryptic exon incorporation (evidence of impaired splicing repression) as identified through RNA sequencing (FIGS. 1-2, FIG. 6). The CTR fusion protein or a control protein with just the N-terminal fragment of TDP-43 alone (NTDP) (FIG. 2A) was then expressed using the binary GAL4/UAS expression system under control of either a restricted motor neuron specific driver D42-Gal4, or an Hsp70-Gal4 driver to achieve ubiquitous expression. We first confirmed the expression and cell localization of the fusion protein to the nucleus, as expected. Whereas NTDP expression under both drivers failed to show any rescue effect, expression of CTR in motor neurons was efficient to mitigate the motility defects (FIG. 2B) and extend the life span to almost 30 days, close to one half of a normal life span (FIG. 2C). Expression of CTR ubiquitously by Hsp70-Gal4 further extended the life span to over 45 days (FIG. 2C).

Figure 2E:
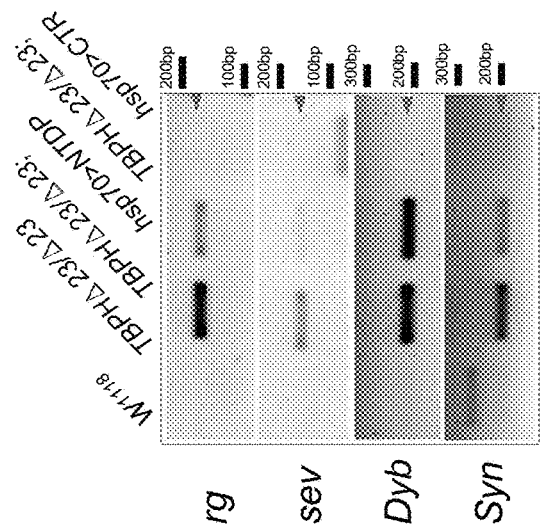
Figure 2D:
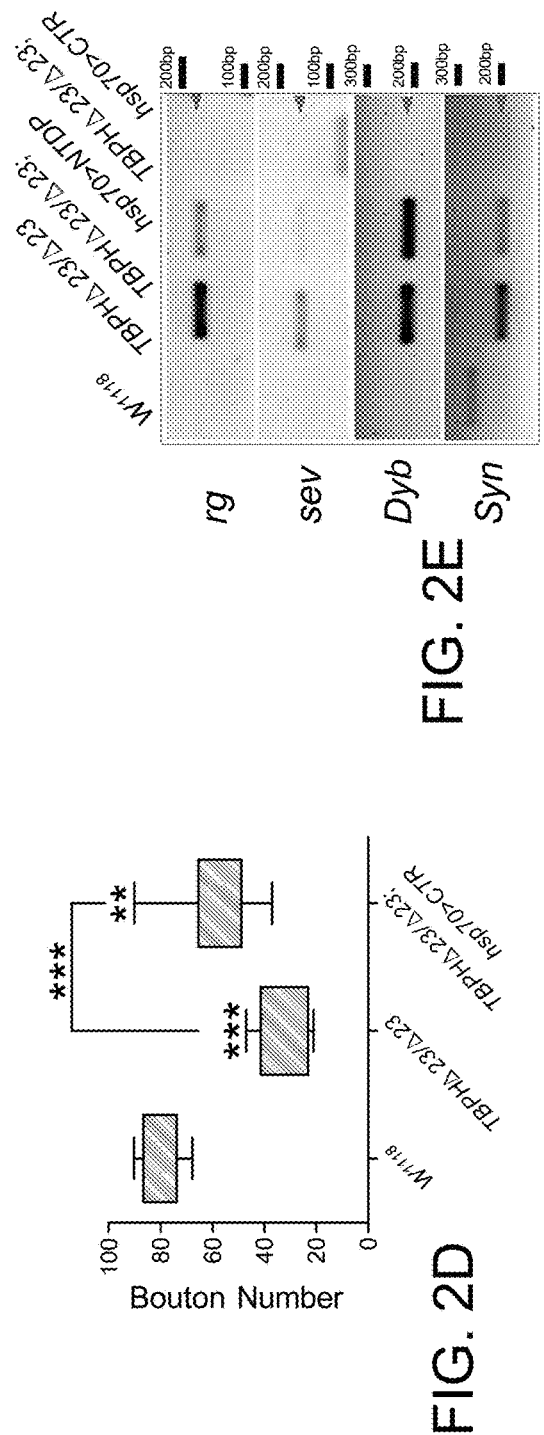

Consistent with previous observations that TBPH is required to form and maintain the presynaptic terminal structures (Feiguin et al., FEBS Lett., 583(10):1586 (2009)), CTR expression resulted in recovery of presynaptic complexity with increased formation of synaptic boutons and axonal terminal branching. Importantly, a subset of splicing abnormalities was restored (FIG. 2E). Together, these results strongly support the idea that splicing repression is a major function of TBPH in motor neurons.

A Therapeutically Relevant Strategy to Restore TDP-43 Mediated Splicing Repression in Mammalian Motor Neurons To establish this notion with TDP-43 in mammalian motor neurons in a therapeutically relevant manner, we took advantage of our Tdp-43 conditional knockout mice, in which exon 3 of Tdp-43 was flanked by loxp sites (Tardbp$^{F/F}$), and crossbred them with a choline acetyltransferase (ChAT) dependent Cre driver line (Rossi et al., Cell Metabolism, 13(2):195 (2011)) (ChAT-IRES-Cre) to generate a line lacking Tdp-43 in >95% of ChAT-positive spinal motor neurons (ChAT-IRES-Cre;Tardbp$^{F/F}$ mice, FIG. 3A). These Tdp-43 conditional knockout mice exhibited progressive motor neuron loss accompanied by reduced body weight, tremor, hindlimb weakness, and paralysis with death occurring around 8-10 months of age. This phenotype is consistent with other, previously reported motor neuron Tdp-43 knockout mouse models. Iguchi et al., Brain: A Journal of Neurology, 136(5):1371 (2013). Because TDP-43 is tightly regulated through an autoregulatory mechanism (Polymenidou et al., Nat Neurosci., 14(4):459 (2011)), TDP-43 levels remained normal and no overt phenotype was observed in mice lacking one allele of Tardbp (ChAT-IRES-Cre;Tardbp$^{F/+}$ heterozygous mice). As predicted, we found evidence of aberrant splicing and cryptic exon incorporation in spinal cords of ChAT IRES-Cre;Tardbp$^{F/F}$ mice (FIG. 5E, red bars).

Figure 3C:
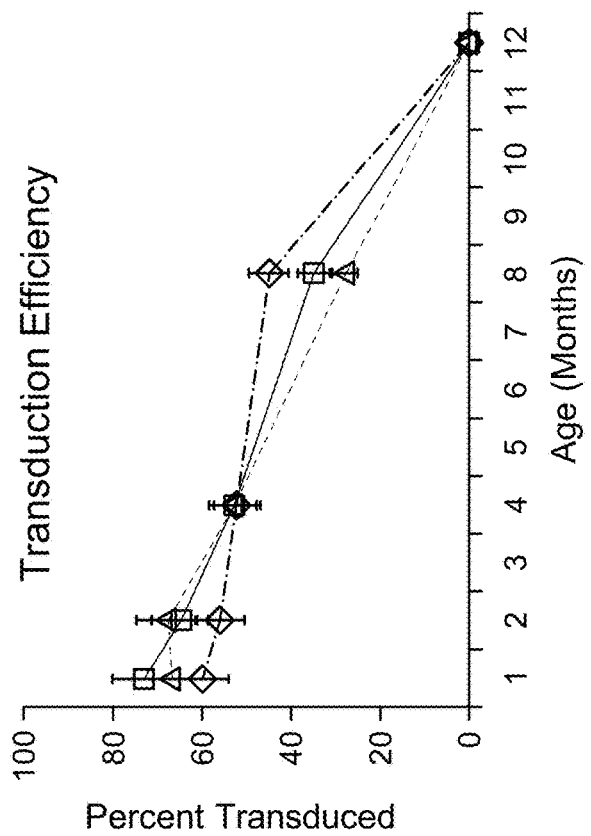
Figure 3D:
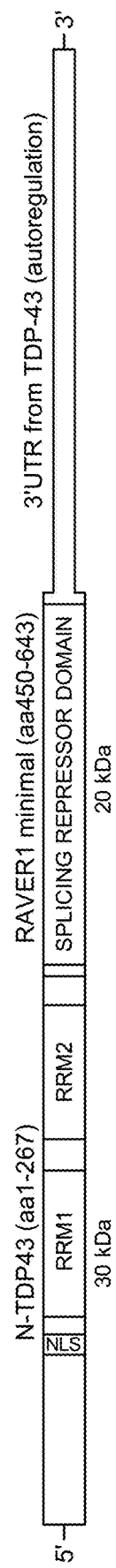
Figure 4A:
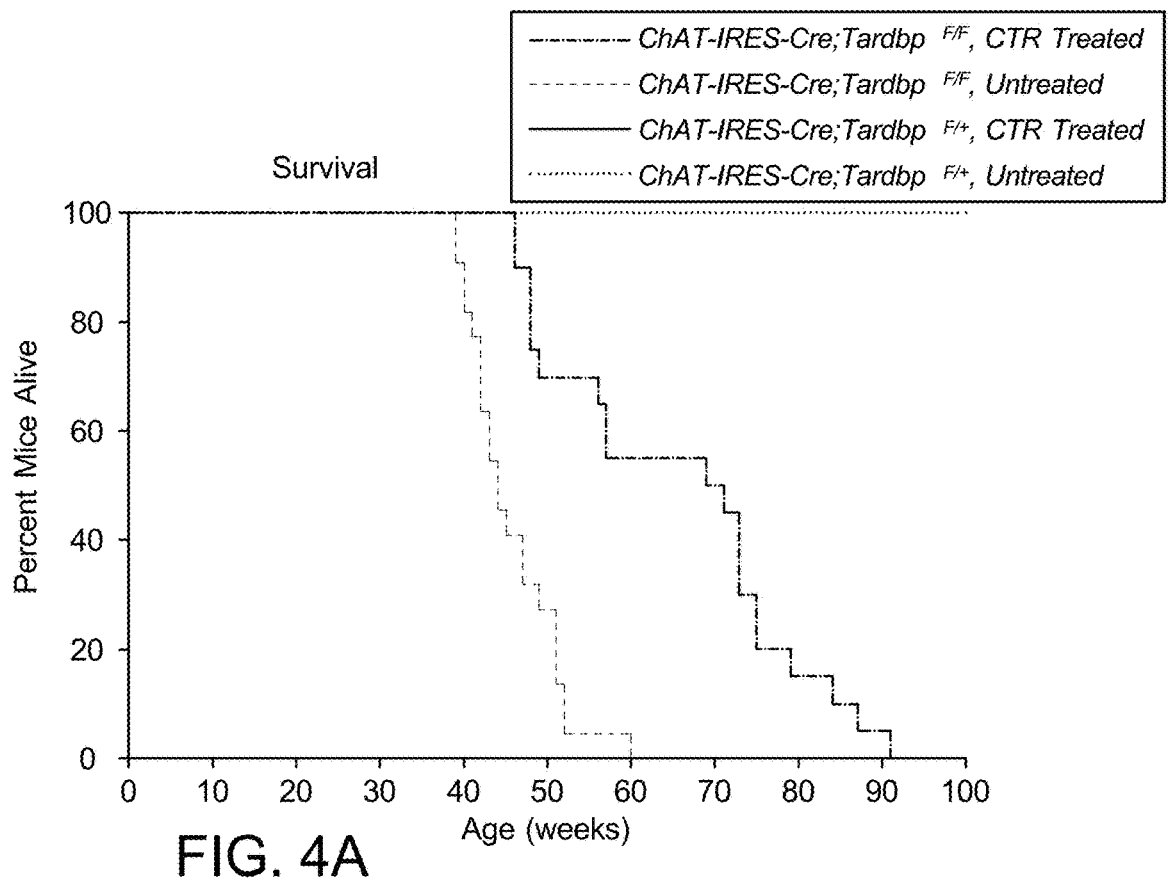
FIGS. 4A-4E Expression of CTR in Tdp-43 knockout mice prolong survival and attenuates behavioral deficits. (A) Kaplan-Meier survival curve of ChAT-IRES-Cre;Tardbp$^{F/+}$ and ChAT-IRES-Cre;Tardbp$^{F/F}$ mice administered AAV9 containing either CTR (treated) or GFP control (untreated). Data from both cohorts are shown together. Median untreated ChAT-5 IRES-Cre;Tardbp$^{F/F}$ survival was extended from 44 weeks to 73 weeks in treated mice (p<0.001 for all analyses). (B) CTR treatment mitigated the age-dependent body weight loss of knockout mice while having no effect on control mice. Hanging wire (C) and rotarod performance (D) show a mitigation of motor deficits in CTR-treated knockout mice compared to untreated controls (*p<0.05,  p<0.01, * p<0.001, Tukey's multiple comparison test). Progression of hanging wire deficits was also significantly attenuated in CTR-treated mice (untreated slope=−1.19, CTR slope=−0.68, p<0.01) (E) Kaplan-Meier survival curve of onset of motor dysfunction, as defined as two consecutive weeks of <60 s hanging wire time. Onset was delayed in CTR-treated knockout mice (median onset: 30 versus 19 weeks, p<0.001).

To establish whether splicing repression is a major function of TDP-43 in mammalian motor neurons, we elected to use AAV9 to deliver CTR to central neurons of mice lacking TDP-43 in spinal motor neurons. Perinatal unilateral intracerebroventricular injection of AAV9 ($3\times10^{10}$ vg/mouse) carrying our CTR chimeric construct under a ubiquitous chicken beta-actin hybrid (CBhA) promoter selected for its small size and robust long-term expression (Kawamoto et al., Molecular Therapy, 11(6):980 (2005)) resulted in CTR protein expression in 50-60% of cervical and lumbar mouse motor neurons that persisted to at least 8 months (FIG. 3C,D). CTR expression was strongest in the nucleoplasm, with no evidence of cytoplasmic CTR aggregates (FIG. 3B). No difference was observed between cervical and lumbar expression efficiency at any age (FIG. 3C) or between ChAT-IRESCre;Tardbp$^{F/+}$ and ChAT-IRES-Cre;Tardbp$^{F/F}$ mice at p30, an early age preceding neuronal loss (FIG. 3B-C). CTR expression had no effect on Cre-mediated Tdp-43 knockout efficiency. While viral transduction was broadly distributed throughout the CNS, no behavioral (FIG. 4) or pathological evidence of acute or chronic toxicity from CTR protein expression was observed in ChAT-IRES-Cre;Tardbp$^{F/+}$ mice within the CNS or any major organ system; these treated ChAT-IRES-Cre;Tardbp$^{F/+}$ mice exhibited a normal lifespan (FIG. 4A).

Figure 4B:
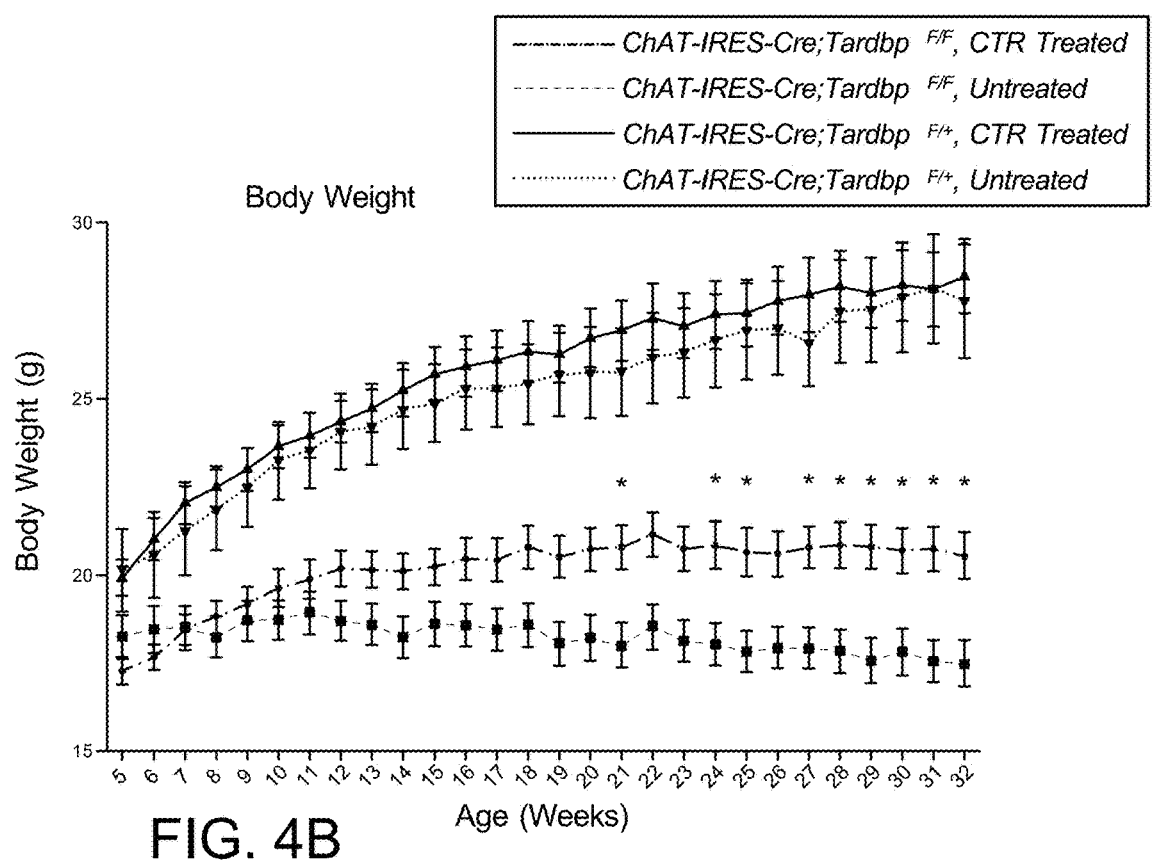
Figure 4C:
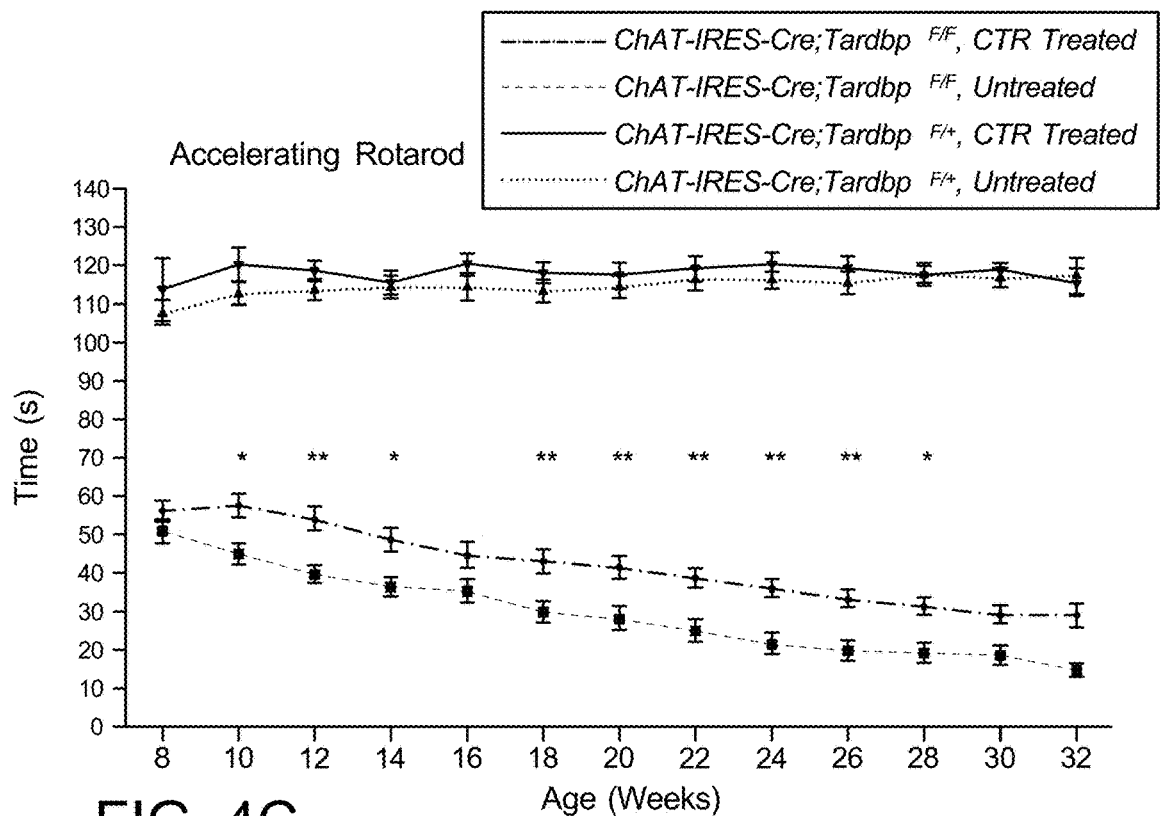
Figure 4D:
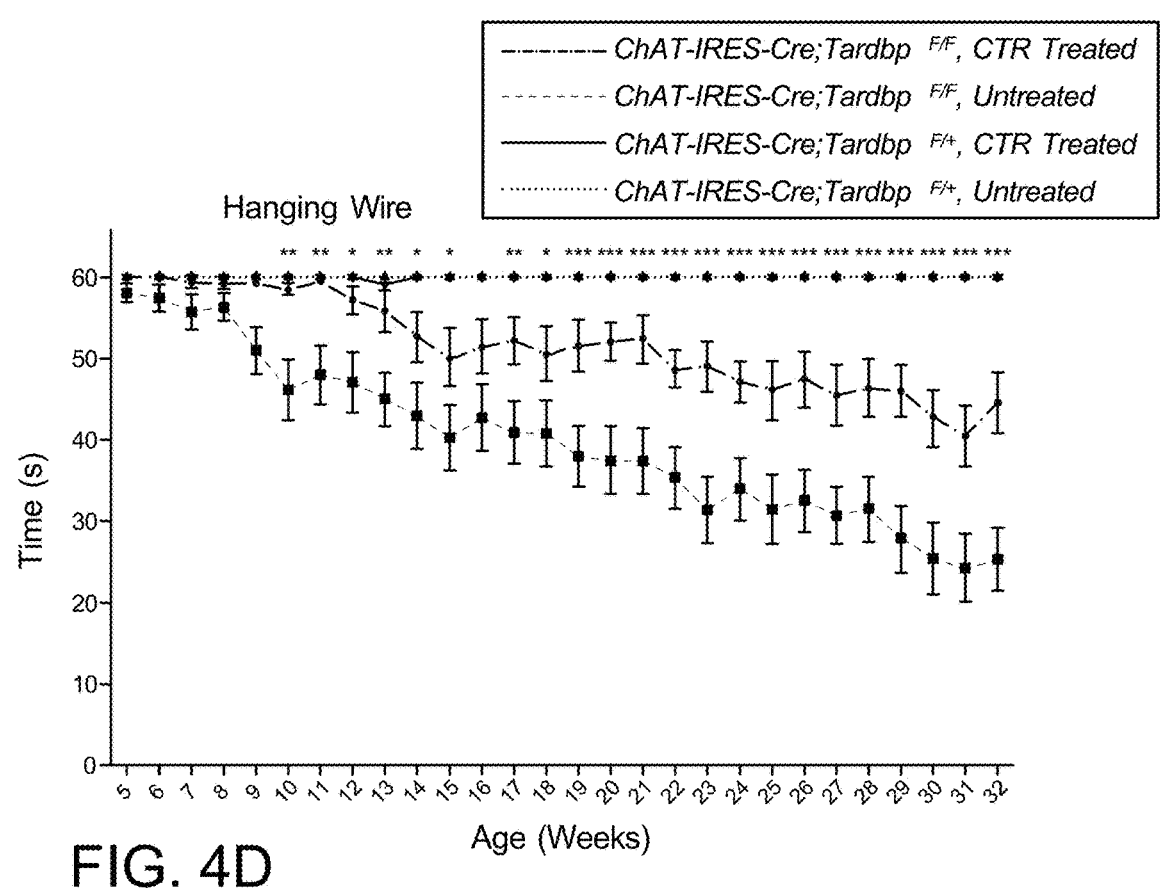
Figure 4E:
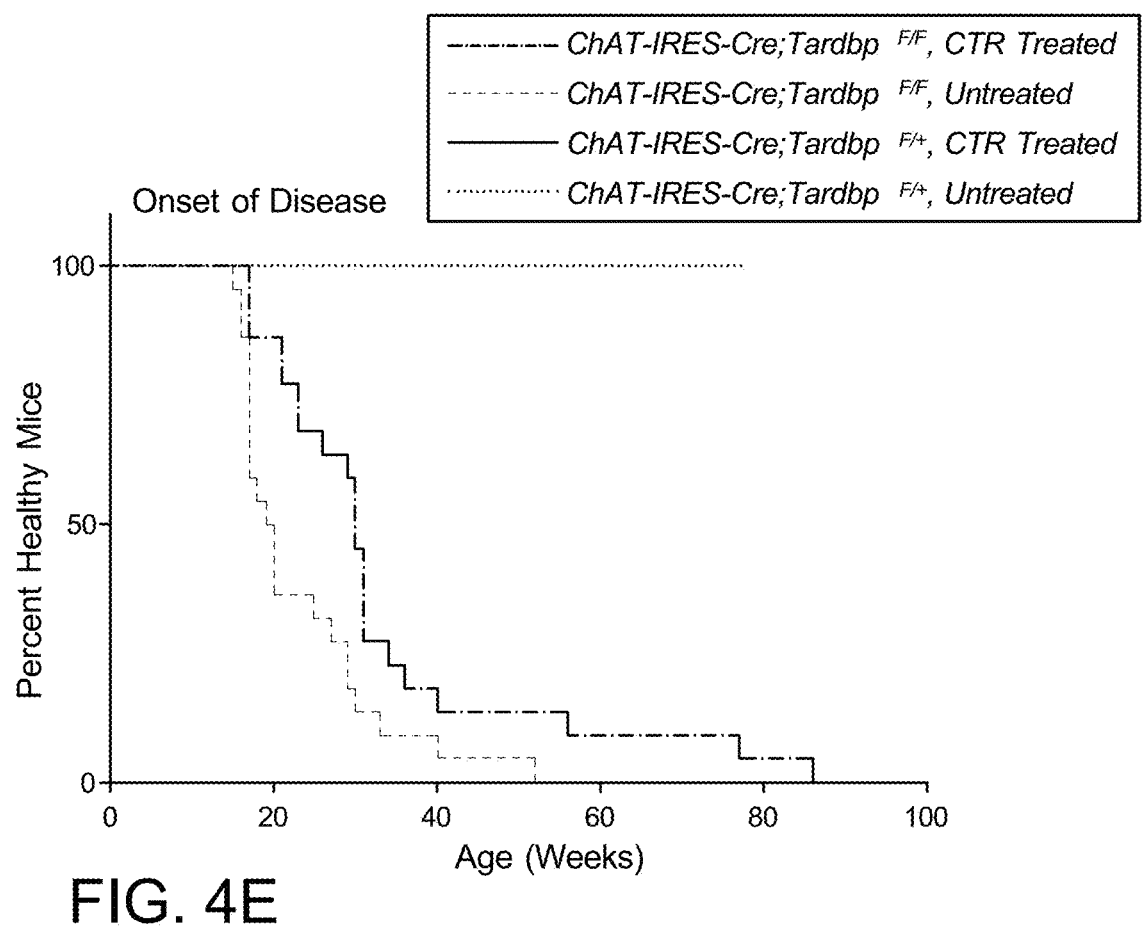

Two cohorts of ChAT-IRES-Cre;Tardbp$^{F/F}$ mice injected with our CTR fusion protein gained greater weight as compared to their untreated breeder-matched knockout controls (FIG. 4B). Treated ChAT-IRES-Cre;Tardbp$^{F/F}$ mice also performed better on the hanging wire and accelerating rotarod tests, with a delayed onset and slower progression of motor deficits (FIG. 4C-E). Consequently, treated ChAT-IRES-Cre;Tardbp$^{F/F}$ mice showed a robust extension of their lifespan, with a median survival increase of 29 weeks (66%) (FIG. 4A). Notably, a cohort of ChAT-IRES-Cre;Tardbp$^{F/F}$ mice treated with just the N-terminal fragment of TDP-43 showed no such motor improvements or weight gain, suggesting that splicing repression, and not some other function of the N-terminal fragment of TDP-43, underlies the rescue effect.

Figure 5D:
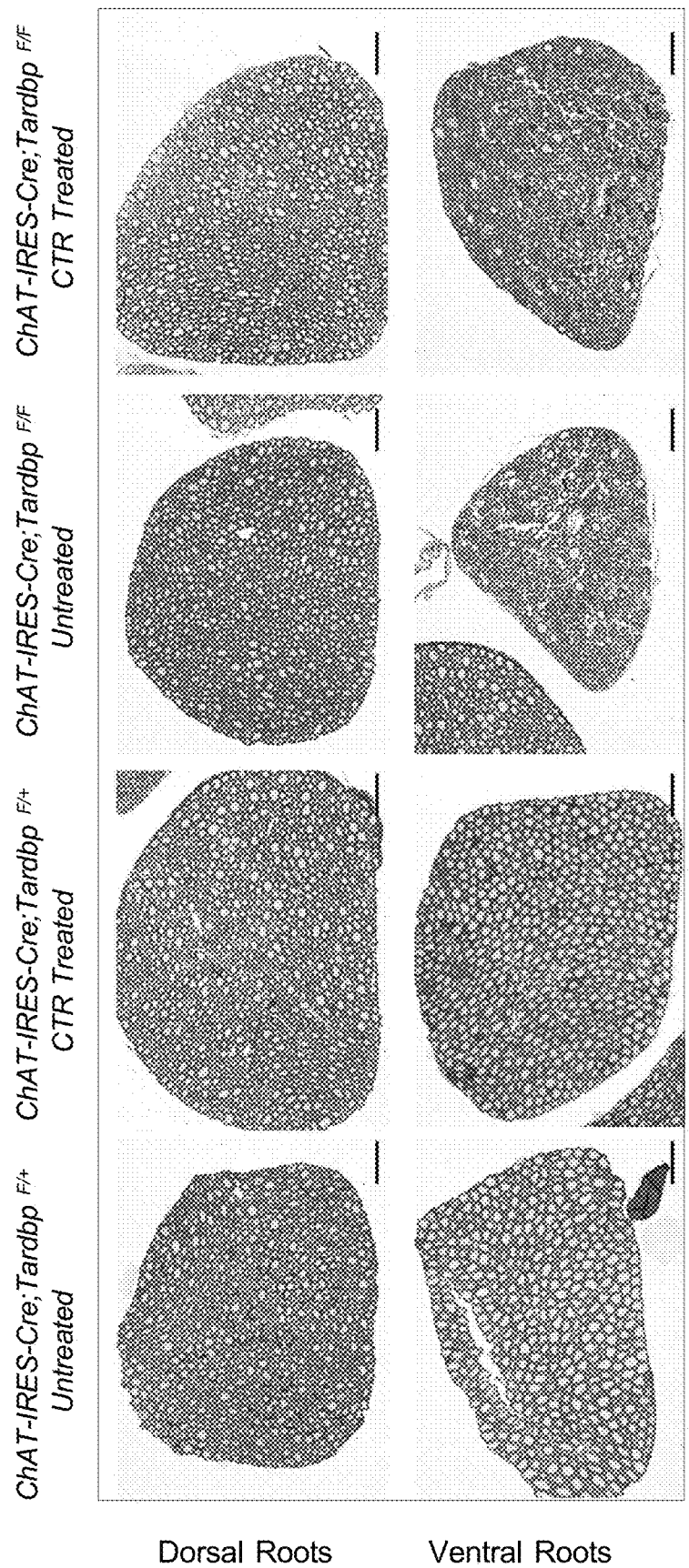
Figure 5E:
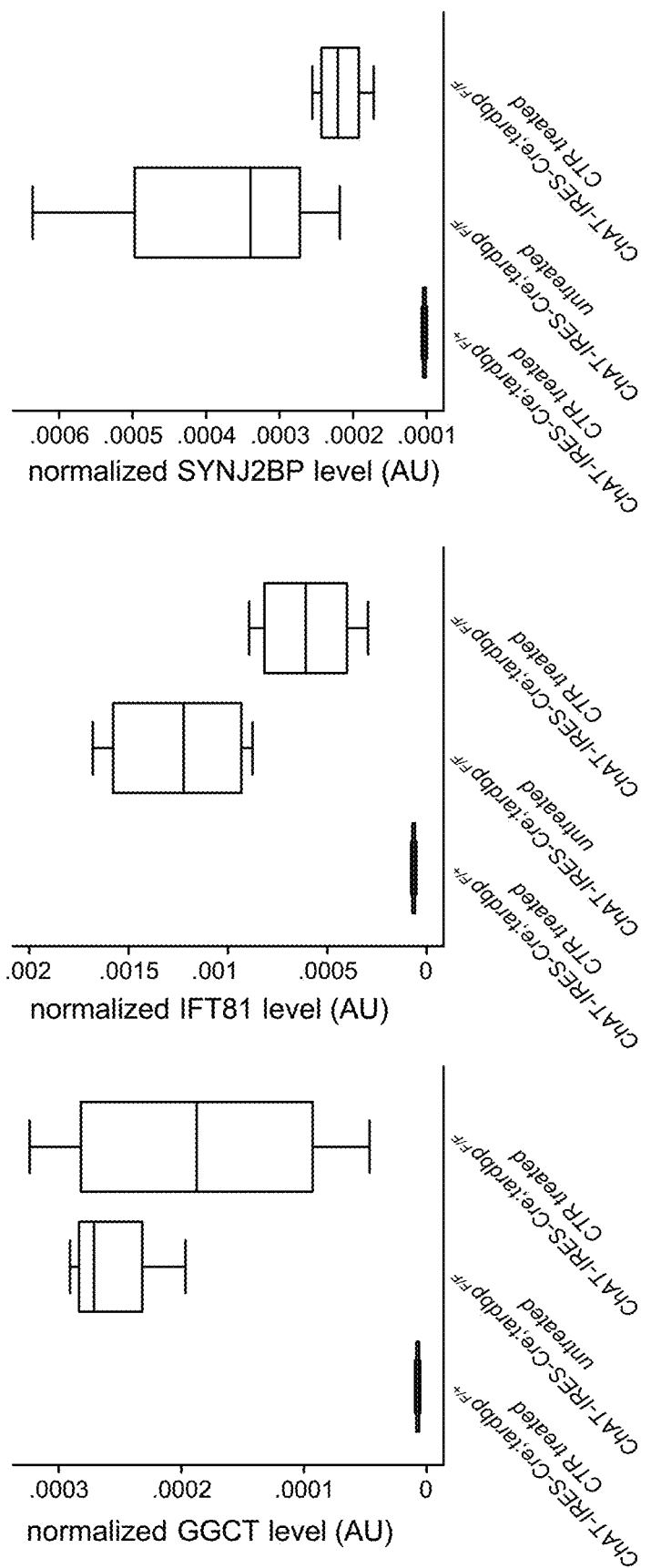

Pathological analysis of 1, 3, and 5-month old cohorts of ChAT-IRES-Cre;Tardbp$^{F/+}$ and ChAT-IRES-Cre;Tardbp$^{F/F}$ mice revealed that while knockout mice lose 50% of ChAT-positive spinal motor neurons between 1 and 3 months' age, CTR treatment significantly mitigated this loss (FIG. 5A, B). Importantly, with our observed transduction efficiency of ~60%, this motor neuron rescue in CTR-treated ChAT-IRES-Cre;Tardbp$^{F/F}$ mice represents about 45% of the predicted maximum cell-autonomous rescue effect (FIG. 5B, dotted line). The observed rescue effect of CTR on spinal motor neurons was most robust at the 3-month timepoint. While the size of L3 dorsal roots remained unchanged, L3 ventral spinal root cross-sectional area was markedly preserved in treated ChAT-IRESCre;Tardbp$^{F/F}$ mice (FIG. 5C-D), corroborating the behavioral benefits offered by the CTR splicing repressor.

While the downstream effects of TDP-43 mediated splicing repression occur on a transcriptome-wide level, we selected three transcripts with cryptic exon incorporation identified through previous RNA seq analysis (Jeong et al., Molecular Neurodegeneration, 12:1 (2017)) to function as a biochemical correlate of TDP-43 mediated splicing repression. As predicted, treatment with our CTR protein significantly rerepressed these aberrant cryptic exon splicing events as determined by quantitative RT-PCR (FIG. 5E). Expression of the N-terminal fragment of TDP-43 alone did not result in any such rerepression, suggesting that CTR expression does not interfere with normal TDP-43 function. Taken together, our results support the notion that splicing repression is a major function of TDP-43 in motor neurons and suggest that loss of this splicing repression could underlie neurodegeneration in diseases such as ALS.

We validate here for the first time that TDP-43 mediated splicing repression is a major function of TDP-43 in motor neurons. Our findings strongly support the idea that compromised transcriptomic integrity following the loss of TDP-43 mediated splicing repression represents a key pathogenic mechanism underlying motor neuron degeneration. As AAV gene therapy holds promise for treatment of human diseases, delivery of our replacement TDP-43 mediated splicing repressor via AAV9 represents a therapeutically relevant strategy to target neurons in human neurodegenerative disease. It will be important in the future to assess the benefit of this therapeutic approach in other ALS-linked models exhibiting loss of nuclear TDP-43 mediated splicing repression, as evidenced by incorporation of cryptic exons in motor neurons. To maximize the benefit of this therapeutic strategy, several factors should be considered: 1) AAV serotypes (Chan et al., Nat Neurosci., 20(8):1172 (2017)) that would provide greater transduction efficiency than that of AAV9, which transduced only about 60 percent of ChAT-positive spinal motor neurons (FIG. 3C); 2) optimization of the splicing repressor domain of RAVER1 to restore all TDP-43 dependent splicing events, as our current construct employed only the minimal domain of RAVER1 (Ling et al., Science, 349(6248):650 (2015)); and 3) increasing the duration of expression of the CTR protein, as the accumulation of this repressor was limited to 8-12 months, which was correlated with the timing of the increase in mortality of CTR-treated Tdp-43 conditional knockout mice (FIG. 4A). Coupled with alternative delivery methods in adult mice, optimization of these factors will further validate our therapeutic approach and help set the stage for future gene therapy trials for ALS.

We previously demonstrated that cryptic exons are highly variable between different cell types and organisms, suggesting that TDP-43 loss may impair cell-type specific pathways in unique ways and complicating efforts at developing treatments targeting any particular downstream pathway. However, the splicing repression function of TDP-43 is highly conserved across species, making our mechanism-based therapeutic approach, which rescues lethality in both *Drosophila* and murine models, a more attractive upstream strategy.

Our results do not exclude other important functions of TDP-43, as this protein has been suggested to be involved in nuclear and non-nuclear cellular processes besides splicing repression, nor do they address the potential toxic effects of cytoplasmic TDP-43 aggregation. White et al., Nat Neurosci., 21(4):552 (2018). Nuclear TDP-43 depletion could be an early pathogenic event, possibly preceding its cytoplasmic aggregation, and while promising therapeutic options for reducing TDP-43 aggregation mediated toxicity are being developed (Becket et al., Nature, 544(7650):367 (2017); Kim et al., Nat Genet., 46(2):152 (2014)), further effort is needed to clarify the different contributions of toxic gain of function and nuclear loss of function of TDP-43 to the pathogenesis of neurodegenerative disease. Assessing the importance of splicing repression as well as the ability of CTR to avoid cytoplasmic sequestration and perform this role in other models of TDP-43 dysfunction will improve our understanding of the complex interplay between cytoplasmic accumulation and nuclear loss of TDP-43.

Example 2: TDP-43 Nonconserved Cryptic Exon as a Biomarker for Sporadic Inclusion Body Myositis In several different neurodegenerative diseases, TDP-43 redistributes from the nucleus to form large ubiquitinated cytoplasmic inclusions; collectively, these diseases are termed TDP-43 proteinopathies. Neumann et al., Science. 314, 130-3 (2006). Missense mutations in TDP-43 are also linked to familial ALS, strongly supporting the idea that TDP-43 proteinopathy is central to the pathogenesis of sporadic disease. Sreedharan et al., Science 319: 1668-1672 (2008). IBM is the most common acquired muscle disease of adults over the age of 50 and typically progresses to major disability. Cox et al., Brain 134 (Pt 11):3167-75 (2011) However, the molecular mechanisms underlying the development and progression of disease are currently unknown. Lloyd T. E., Curr Opin Rheumatol. 22:658-64 (2010) Our previous demonstration that TDP-43 repression of nonconserved cryptic exons is compromised in neurodegenerative disease would suggest a common pathogenic mechanism with IBM. Ling et al., Science. 349, 650-655 (2015).

Figure 7C:
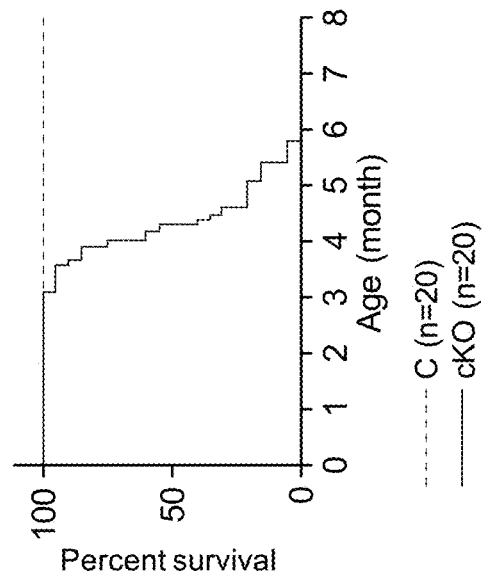
Figure 7B:
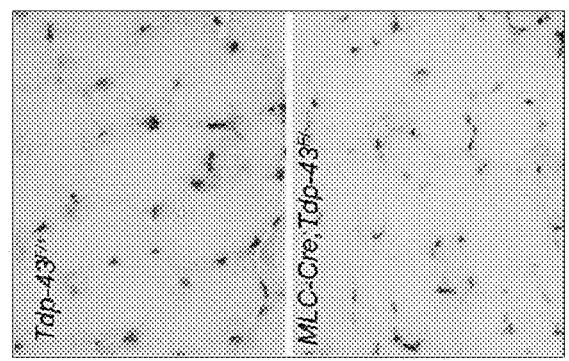
Figure 7A:
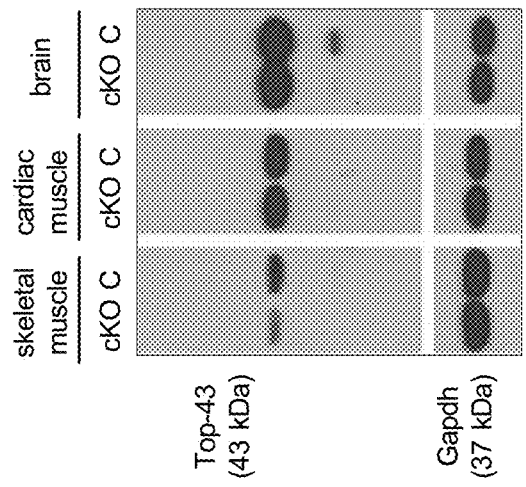

To test whether loss of TDP-43 function contributes to the pathogenesis of IBM, we generated mice lacking Tdp-43 in skeletal muscle (termed MLC-Cre;Tdp-43$^{F/-}$) from Tdp-43loxP/loxP (Chiang et al., Proc. Natl. Acad. Sci. U.S.A. 107, 16320-4 (2010)), Tdp-43$^{F/+}$ and MLC-Cre (Mourkioti et al, Genesis 46:424-430 (2008)) mice. The level of Tdp-43 was substantially reduced in skeletal muscle of MLC-Cre; Tdp-43$^{F/-}$ mice when compared to that of MLCCre;Tdp-43$^{F/+}$ and Tdp-43$^{F/+}$ control mice, but remained unaffected in cardiac muscle and brain (FIG. 7A). Immunohistochemical analysis of skeletal muscle with antisera directed against Tdp-43 confirmed the reduced expression of Tdp-43 in MLC-Cre;Tdp-43$^{F/-}$ mice (FIG. 7B). Both MLC-Cre;Tdp-43$^{F/-}$ as well as control MLC-Cre;Tdp-43$^{F/+}$, Tdp-43$^{F/+}$ and Tdp-43$^{F/-}$ littermates showed comparable growth and development into early adult. However, from 2.5 months in age, MLC-Cre;Tdp43$^{F/-}$ mice showed a dramatic reduction in body weight reaching end stage within 6 weeks after onset of weight loss. Kaplan-Meier analysis of a cohort of mice indicates a median survival of 130 days for MLC-Cre;Tdp-43$^{F/-}$ mice, while control littermates survived well past the span of the experiment (FIG. 7C).

Pathological analyses of 3-month-old MLC-Cre;Tdp-43$^{F/-}$ mice showed striking skeletal muscle atrophy. Histological analyses of skeletal muscle from MLC-Cre;Tdp-43$^{F/-}$ mice showed fibers with hypercellularity, large variability in size and increased numbers of atrophic myofibers. There was marked atrophy as evidenced by fibers that are rounded with loss of striation (FIG. 7D). Importantly, analyses of skeletal muscle from MLCCre;Tdp-43$^{F/-}$ mice revealed striking numbers of red-rimmed vacuoles, a defining feature of IBM (Askanas V. & Engel W. K., Current Opinion in Rheumatology 10:530-542 (1998)) and myofibrillar disruption and uneven distribution of mitochondria (FIG. 7D).

Importantly, abnormal accumulation of p62+ inclusions was observed within the myofibers of MLC-Cre;Tdp-43$^{F/-}$ mice (FIG. 7C), a pathology that is frequently seen in IBM. Ultrastructure analyses of quadriceps and gastrocnemius muscles demonstrated substantial pathology in MLC-Cre; Tdp-43$^{F/-}$ mice compared to controls. In control Tdp43$^{F/+}$ mice, myocytes show regular banding pattern with morphologically normal mitochondria located adjacent to the Z disks; and each myocyte had a peripherally located nucleus (FIG. 7E). In contrast, mice lacking Tdp-43 in skeletal muscle had large numbers of myocytes with disintegrated myofilament, widespread disruption of Z-disks, and one or more centrally located nuclei (FIG. 7F). Notably, marked redistribution of mitochondria into aggregates which tended to accumulate around amorphous deposits was frequently seen, and many of the mitochondria were giant and swollen with degenerate cristae (FIG. 7F). The presence of a large number of abnormal mitochondria is suggestive of a defect in mitophagy—the selective autophagy of damaged mitochondria. Vacuoles can be seen in some fibers, although it is unclear whether these are lysosomal in nature or reflect swollen mitochondria with degenerate cristae (FIG. 7F). Importantly, the abnormal accumulation and degeneration of mitochondria described in MLC-Cre;Tdp-43$^{F/-}$ mice have also been reported in IBM muscle biopsies. Oldfors et al., Neurology 66:S49-55 (2006). Collectively, immunohistological and ultrastructural data show pathological features that are characteristic of IBM, and strongly support the idea that the myopathy observed in MLC-Cre;Tdp-43$^{F/-}$ mice resembles that of IBM.

To develop a TDP-43 associated biomarker for IBM, we took a two-prong approach to identify cryptic exon targets from human myoblasts and skeletal muscles of IBM patient. Using the siRNA (FIG. 8A) strategy that we previously performed for HeLa cells (Ling et al., Science, 349, 650-655 (2015)), we depleted TDP-43 from human cultured myoblasts. Total RNAs extracted from these TDP-43 deficient myoblasts were subjected to RNA-seq analysis. As expected, we identified a set of RNA targets in which non-conserved cryptic exons were contained or flanked by "UG" repeats. As was shown for HeLa cells, we identified, in addition to cassette exons, a subset of non-standard cryptic exons that could be categorized as alternative transcriptional start sites, premature polyadenylation sites, or expansions of conserved canonical exons (FIG. 8B). These results establish that TDP-43 represses non-conserved cryptic exons in human myoblasts and support the notion that TDP-43 loss-of-function could contribute to the pathogenesis of IBM.

Figure 8G:
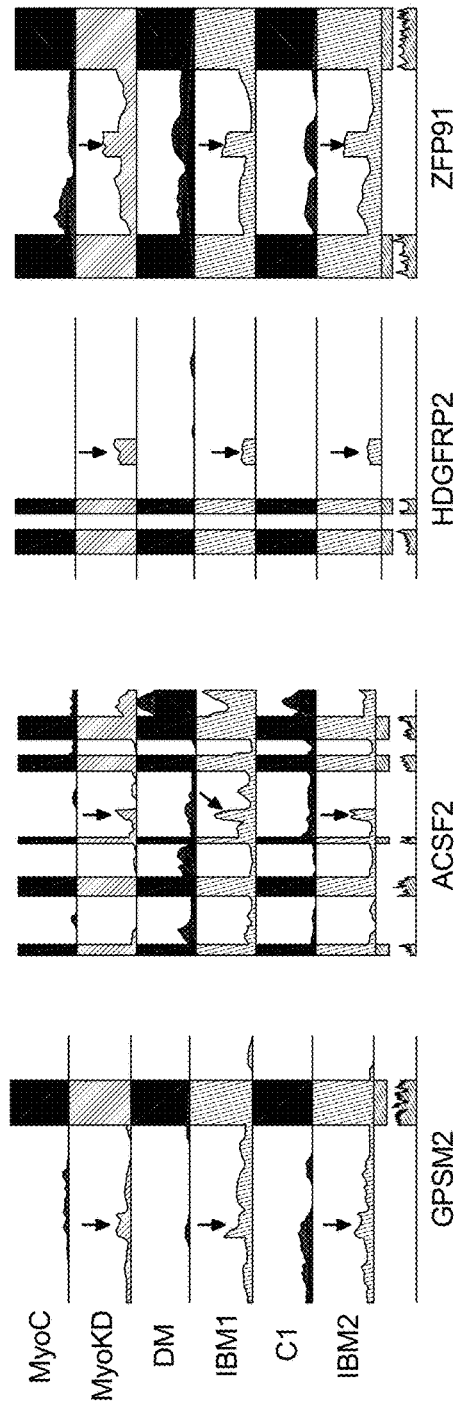
Figure 8H:
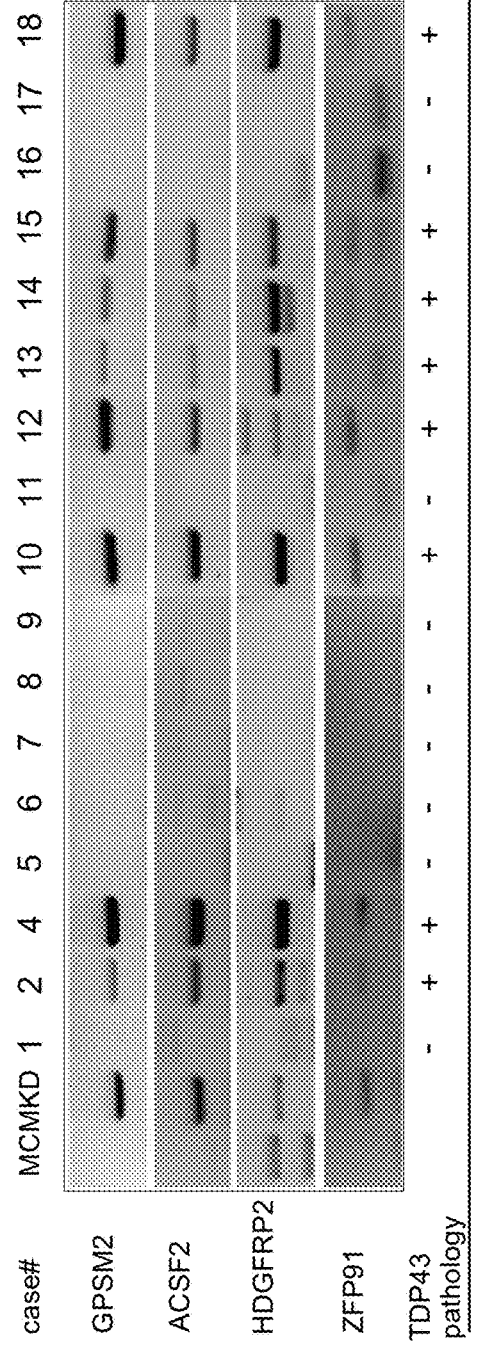

If loss of TDP-43 function indeed occurs in IBM, we predict that there will be incorporation of nonconserved cryptic exons in skeletal muscles of IBM patients. To directly assess whether repression of cryptic exons is compromised in IBM, we first confirmed the diagnosis from muscle biopsies of cases that exhibit pathological hallmarks of IBM, including rimmed vacuoles, endomysial inflammation, and p62 and TDP-43 positive protein aggregates. Interestingly, besides the abnormal cytoplasmic accumulation of TDP-43 (FIG. 8D), we also found clearance of TDP-43 from nuclei in surrounding but otherwise morphologically normal myofibers (FIG. 8E-F). Total RNA from biopsies of quadriceps muscle from two IBM patients (case 4 and case 18), along with two controls, were extracted and subjected to RNA-seq analysis. Importantly, we found several nonconserved cryptic exons in two IBM cases but not in a DM or "mild, nonspecific atrophy" control case (FIG. 8G). To screen for incorporation of cryptic exons as biomarkers for IBM, total RNA from quadriceps muscle biopsies from a small cohort of IBM cases and controls were extracted and subjected to RT-PCR analysis. Moreover, RT-PCR products were subjected to DNA sequencing to confirm amplification across cryptic exon junctions. We selected initially a panel of four RNA targets (GSPM2, ACSF2, HDGFRP2, ZFP91) for our analysis. Importantly, we were able to discriminate all other IBM cases in the cohort from controls using this panel of nonconserved cryptic exons (FIG. 8H). Sequence and alignment validation of cryptic exon RT-PCR products were performed for the RNA targets (GSPM2, ACSF2, HDGFRP2, ZFP91). Taken together, these data suggest that TDP-43 repression of nonconserved cryptic exons is compromised in skeletal muscles of IBM and identify a biomarker for the diagnosis of IBM.

Mislocalization of RNA binding proteins, such as TDP-43, have been documented within muscle fibers of patients with various forms of myopathies, a progressive inflammatory skeletal muscle disease characterized by rimmed vacuoles and inclusion bodies. Salajegheh et al., Muscle Nerve 40:19-31 (2009) The discovery of two other hnRNPs linked to multisystem proteinopathy (Kim et al., Nature 495:467-73 (2013)), disorders that include the presence of rimmed vacuoles, has led to the identification of abnormal distribution of hnRNPA1 and hnRNPA2B1 in IBM. Pinkus et al., Neuromuscular Disorders 24:611-6 (2014). These observations suggest that aspects of RNA metabolism are perturbed in IBM. Our findings that depletion of TDP-43 from skeletal muscles of mice or humans led to a failure to repress cryptic exons indicates that loss of nuclear TDP-43 function could contribute to the pathogenesis of IBM.

Neither an effective therapy nor a functional biomarker is available for IBM. Our discovery of a panel of TDP-43 nonconserved cryptic exons as a diagnostic biomarker will facilitate future efforts to develop surrogate endpoints for IBM clinical trials. Moreover, we have identified a therapeutic approach to prevent incorporation of cryptic exons in cells lacking TDP-43 using a TDP-43-RAVER1 fusion protein capable of repressing cryptic exons and prevent cell death. In order to translate this novel finding into the clinic, it will be necessary to validate this therapeutic strategy using a mouse model system. For this purpose, our conditional Tdp-43 knockout mice lacking Tdp-43 in their myofibers will be employed to validate that correction of splicing abnormalities rescues pathologic features of IBM.

Methods

Mouse Model

Tdp-43$^{F/F}$ and Tdp-43$^{+/-}$ mice were previously generated in our laboratory as described. Tdp$^{+/-}$ mice were bred with MLC-Cre mice to generate MLC-Cre;Tdp-43$^{+/-}$ mice, which were then crossed with Tdp-43$^{F/F}$ mice to generate MLC-Cre;Tdp-43$^{F/-}$ mice. Littermates of the cross (Tdp-43$^{F/+}$) were used as control mice for the experiments performed. DNA extracted from ear punches of mice was genotyped by PCR using the following set of primers: Tdp-43 floxed (forward 5'-AAC TTC AAG ATC TGA CAC CCT CCC C-3' and reverse 5'-GGC CCT GGC TCA TCA AGA ACT G-3'), Tdp-43 wild-type/knockout (forward 5'-TCT TAC AAT GCC TGG CGT GGT G-3' and reverse 5'-CGT GGT TGC GCA CCC TAA CTA TAA-3'), and MLC-Cre (forward 5'-AAG CCC TGA CCC TTT AGA TTC CAT TT-3' and reverse 5'-AAA ACG CCT GGC GAT CCC TGA AC-3'). All procedures involving mice were performed under the guidelines of the Johns Hopkins Medical Institutions Animal Care and Use Committee.

Muscle Biopsies

Studies were performed on fresh-frozen diagnostic muscle biopsies obtained, with informed consent, from 8 IBM and 9 control patients (4 dermatomyositis, 1 normal, 2 mild, nonspecific atrophy, 1 mild neurogenic atrophy and 1 moderate neurogenic atrophy). The average age of IBM patients was 63 years (median 64); the average age of control patients was 63 (median 63). All muscle biopsies are taken from the rectus femoris quadriceps muscle. All IBM cases met ENMC 2011 criteria for clinically defined IBM, and DM cases met Bohan and Peter criteria.

Histology and Immunohistochemistry

Tissues were dissected and flash frozen in freezing isopentane. Cryosections were cut at 10 μm thickness and stained according to standard protocols. Antibodies used for immunohistochemistry were: rabbit anti-p62 (Santa Cruz Biotechnology H-290), mouse anti-ubiquitin (Dako Z0458) and rabbit anti-TDP-43 (Proteintech 10782-2-AP and 12892-1-AP). The immunoreactivity was visualized using the Vectastain ABC Kit and diaminobenzidine peroxidase substrate (Vector Laboratories). Images were obtained using an Olympus BX53 microscope.

Electron Microscopy

Mice were anesthetized by an intra-peritoneal injection of 15% chloral hydrate and perfused with 4% paraformaldehyde in 0.1M phosphate buffer (pH 7.4). Muscle was removed and post-fixed with 4% paraformaldehyde with 2% glutaraldehyde in 0.1M phosphate buffer (pH 7.4) overnight. Tissues were then washed in PBS, dehydrated and embedded in Epon. Thick (1 μm) and thin (100 nm) sections were stained respectively with toluidine blue and lead citrate/uranyl acetate. The images were obtained using a Hitachi 7600 transmission electron microscope.

Cell Culture and Manipulation

Human skeletal myoblast cells were obtained from Zen-Bio (SKB-F) and cultured as described in Skeletal Muscle Cell Growth Medium (Zen-Bio, SKM-M). Knockdown of TDP-43 was performed by transfecting siRNA targeting the TARDBP transcript (Sigma-Aldrich, EHU109221) while control was transfected with negative control siRNA (LifeTech., 4390843). Transfection of siRNA was achieved using Viromer Blue (Lipocalyx, VB-01LB-01).

Protein Blot Analysis

Proteins from cell culture samples were extracted in RIPA buffer (Sigma). Muscle tissues were snap frozen and manually homogenized in RIPA buffer (Sigma) containing an EDTA-free protease inhibitor cocktail (Thermo Scientific). Protein concentration was determined using the BCA assay (Pierce). Proteins were resolved using the NuPAGE 4-12% Bis-Tris Gel (Novex) with NuPAGE MES SDS Running Buffer (Novex), and -transferred to PVDF membrane (Millipore) with NuPAGE Transfer Buffer (Invitrogen). Primary antibodies used for protein blot analyses were: rabbit anti-TDP-43 (Proteintech 10782-2-AP and 12892-1-AP), mouse anti-GAPDH (Sigma Aldrich), rabbit anti-MAPLC3 (Sigma Aldrich), rabbit anti-Atg7 (Sigma Aldrich), rabbit anti-Atg5 (Proteintech), rabbit anti-Atg3 (Proteintech) and rabbit anti-p62 (Proteintech).

RNA Extraction and RNA-Seq Analysis

RNA was extracted from cell culture samples using TRIzol (Life Tech., 15596-026) and RNeasy Mini Kits (Qiagen, 74104). RNA from human brain tissue was extracted in a similar fashion but required an additional homogenization step (trituration using 1 mL syringe w/20-gauge needle) after placing tissue in TRIzol. Fastq files were aligned to the human genome (hg19 assembly) using HISAT2 and gene abundances were calculated using Cufflinks. Trapnell et al., Nat. Protoc. 7: 562-578 (2012). Cryptic exons were identified by processing BAM files generated from HISAT2 with StringTie (Pertea et al., Nature Biotechnology 33, 290-295 (2015)), a transcript assembly software. Novel exons were identified in StringTie GTF outputs and relative read depths and splice junction coverages for each novel exon were calculated between control and TDP-43 knockdown conditions. Cryptic exons in the myoblast TDP-43 knockdown RNA seq data were then manually curated as previously described. Ling et al., Science. 349, 650-655 (2015).

RT-PCR cDNA was derived from transfected myoblast cell culture and human muscle tissue total RNA (1 μg total RNA/20 μl first strand cDNA reaction) using ProtoScript II (NEB, E6560S). Numerous primers were designed against cryptic exon targets and then screened to identify primer pairs that minimized background bands. Primers that amplify cryptic exon junctions in GPSM2 (199 bp), HDGFRP2 (231 bp), ACSF2 (169 bp), and ZFP91 (118 bp) are listed in Table 1 below:

TABLE 1

| | |
|---|---|
| GPSM2-Forward | AGTGGACATGTGGTGGTAAGAA |
| GPSM2-Reverse | GCTTCAAAGAATGACACGCCA |
| HDGFRP2-Forward | CCTGCGCTAAAGATGTCGGT |
| HDGFRP2-Reverse | ATGCCCCTTTCCAAACCAGAT |
| ACSF2-Forward | TGGTCAGACACAAACCTGG |
| ACSF2-Reverse | ACCGAGATGACTGTGGTCAG |
| ZFP91-Forward | GGCCTTCAAGAGTTCCCACA |
| ZFP91-Reverse | GGATTGGGAAATGTTACTAGATGG |

PCR reactions were performed using DreamTaq Green PCR Mastermix (ThermoFisher, K1081) with the following protocol:

| | |
|---|---|
| Initial Denaturation: | 98° C. for 30 s |
| 42 Cycles: | 98° C. for 30 s |
| | 98° C. for 8 s |
| | 63° C. for 12 s |
| | 72° C. for 30 s |
| Final Extension: | 72° C. for 7 min |
| Hold: | 4° C. |

PCR products were then gel excised and DNA extracted using the QIAquick Gel Extraction Kit (Qiagen, 28704). Sanger sequencing was performed with the 3730x1 DNA Analyzer (Applied Biosystems) and then aligned using UCSC Blat to ensure that the amplified product originated from cryptic exon splicing.

Statistical Analysis

Quantitative data were analyzed using Excel and GraphPad Prism using two-way analysis of variance (ANOVA) test for body weights, and the unpaired t test for strength and rotarod measurements. Data were expressed as the mean, and error bars indicate the Standard Error of the Mean (SEM).

Example 3: Research Plans

See the Appendix included with this application, which describes additional work being carried out by the inventors.

The complete disclosure of all patents, patent applications, and publications, and electronically available material cited herein are incorporated by reference. The foregoing detailed description and examples have been given for clarity of understanding only. No unnecessary limitations are to be understood there from. The invention is not limited to the exact details shown and described, for variations obvious to one skilled in the art will be included within the invention defined by the claims.

What is claimed is:

1. An adeno-associated virus or vector that further comprises a non-native nucleotide sequence capable of expressing a chimeric protein comprising an N-terminal nucleotide binding domain of transactivation response element DNA-binding protein (TDP-43), a C-terminal domain derived from a splicing repressor, and an autoregulatory element, wherein the autoregulatory element comprises SEQ ID NO: 3.

2. The adeno-associated virus or vector of claim 1, wherein the adeno-associated virus or vector is AAV9 or AAVPhP.eB.

3. The adeno-associated virus or vector of claim 1, wherein the splicing repressor is ribonucleoprotein PTB-binding 1 (RAVER1).

4. The adeno-associated virus or vector of claim 3, wherein the splicing repressor is the minimal repressor domain of RAVER1 consisting of SEQ ID NO: 4.

5. The adeno-associated virus or vector of claim 1, wherein the non-native nucleotide sequence comprises SEQ ID NO: 2.

6. An adeno-associated virus or vector that further comprises a non-native nucleotide sequence capable of expressing a chimeric protein comprising an N-terminal nucleotide binding domain of transactivation response element DNA-binding protein (TDP-43), a C-terminal domain derived from a splicing repressor, and an autoregulatory element, wherein the N-terminal nucleotide binding domain of TDP-43 comprises SEQ ID NO: 1.

7. The adeno-associated virus or vector of claim 6, wherein the adeno-associated virus or vector is AAV9 or AAVPhP.eB.

8. The adeno-associated virus or vector of claim 6, wherein the splicing repressor is ribonucleoprotein PTB-binding 1 (RAVER1).

9. The adeno-associated virus or vector of claim 8, wherein the splicing repressor is the minimal repressor domain of RAVERI consisting of SEQ ID NO: 4.

10. The adeno-associated virus or vector of claim 6, wherein the non-native nucleotide sequence comprises SEQ ID NO: 2.

* * * * *

SEQUENCE LISTING

<160> NUMBER OF SEQ ID NOS: 83

<210> SEQ ID NO 1
<211> LENGTH: 268
<212> TYPE: PRT
<213> ORGANISM: Homo sapiens

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Met Ile Asp Gly Arg Trp Cys Asp Cys Lys Leu Pro Asn
                165                 170                 175

Ser Lys Gln Ser Gln Asp Glu Pro Leu Arg Ser Arg Lys Val Phe Val
            180                 185                 190

Gly Arg Cys Thr Glu Asp Met Thr Glu Asp Glu Leu Arg Glu Phe Phe
        195                 200                 205

Ser Gln Tyr Gly Asp Val Met Asp Val Phe Ile Pro Lys Pro Phe Arg
    210                 215                 220

Ala Phe Ala Phe Val Thr Phe Ala Asp Asp Gln Ile Ala Gln Ser Leu
225                 230                 235                 240

Cys Gly Glu Asp Leu Ile Ile Lys Gly Ile Ser Val His Ile Ser Asn
                245                 250                 255

Ala Glu Pro Lys His Asn Ser Asn Arg Gln Arg His
            260                 265

<210> SEQ ID NO 2
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgtctgaat atattcgggt aaccgaagat gagaacgatg agcccattga ataccatcg      60 gaagacgatg ggacggtgct gctctccacg gttacagccc agtttccagg ggcgtgtggg    120
cttcgctaca ggaatccagt gtctcagtgt atgagaggtg tccggctggt agaaggaatt    180
ctgcatgccc cagatgctgg ctggggaaat ctggtgtatg ttgtcaacta tccaaaagat    240

```
aacaaaagaa aaatggatga gacagatgct tcatcagcag tgaaagtgaa aagagcagtc      300
cagaaaacca gcgacctgat tgtcctgggt ctcccatgga aaacaaccga acaggacctg      360
aaagagtatt ttagtacctt tggagaagtt cttatggtgc aggtcaagaa ggacttgaag      420
acaggacata gcaaggggtt tggctttgtt cgttttacgg aatatgaaac acaagtgaaa      480
gtaatgtcac agcgacatat gatagatgga cgatggtgtg actgcaaact tcctaattct      540
aagcaaagcc aagatgagcc tttgagaagc agaaaagtgt tgtggggcg ctgtactgag       600 gacatgactg aggatgagct gcgggagttc ttctctcagt acggggatgt gatggatgtc      660
ttcatcccca agccattcag ggcctttgcc tttgttacat ttgcagatga tcagattgcg      720
cagtctcttt gtggagagga cttgatcatt aaaggaatca gcgttcatat atccaatgcc      780
gaacctaagc acaatagcaa tagaacgcgt ggcaagcctc cacctctgct gccatccgtg      840
cttggacctg ctggaggtga cagagaggct ctgggcttgg gtcctccagc agctcagctc      900
actcctccac cagcacctgt gggactccga ggctctggcc tcagaggcct ccagaaagac      960
agtgggcctc tgccgacgcc tcctggagtc tcactgctgg agaacctcc taaggactac      1020 cggattccac tgaatcccta cctgaaccta cacagcctgc tccctgccag caacctggcg     1080
ggtaaggaag ctagaggctg ggaggcgcc ggaagaagcc gccgcccagc tgagggccct      1140
ccaactaacc ctccagcacc tggaggtggc agcagcagca gcaaagcctt ccagctcaag     1200
tctcgcctgc tcagtccact cagcagcgca cgcctgcctc ctgaaccagg actgtctgac     1260
agctacagct tcgactatcc ctcggacatg ggacctagac ggctcttcag ccacccacgg     1320
gaaccagccc ttgggcctca cggacccagc cgacacaaga tgtctcctcc accaagtggc     1380
ttcggcgaac ggtag                                                      1395

<210> SEQ ID NO 3
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tgcccagtct ctttgtggag aggatttgat cattaaagga atcagcgtgc atatatccaa       60
tgctgaacct aagcataata gcaatagaca gttagaaaga agtggaagat tggtggtaa      120 tccaggtggc tttgggaatc agggtggtt tggtaacagt agaggggtg gagctggctt      180 gggaaataac cagggtggta atatgggtgg agggatgaac tttggtgctt ttagcattaa      240
cccagcgatg atggctgcgg ctcaggcagc gttgcagagc agttggggta tgatgggcat      300
gttagccagc cagcagaacc agtcgggccc atctgggaat aaccaaagcc agggcagcat      360
gcagagggaa ccaaatcagg cttttggttc tggaaataat tcctacagtg gttctaattc      420
tggtgccc                                                               428

<210> SEQ ID NO 4
<211> LENGTH: 194
<212> TYPE: PRT
<213> ORGANISM: Homo sapiens

<400> SEQUENCE: 4

Gly Lys Pro Pro Pro Leu Leu Pro Ser Val Leu Gly Pro Ala Gly Gly
1               5                   10                  15
```

```
Asp Arg Glu Ala Leu Gly Leu Gly Pro Pro Ala Ala Gln Leu Thr Pro
             20                  25                  30

Pro Pro Ala Pro Val Gly Leu Arg Gly Ser Gly Leu Arg Gly Leu Gln
         35                  40                  45

Lys Asp Ser Gly Pro Leu Pro Thr Pro Pro Gly Val Ser Leu Leu Gly
 50                  55                  60

Glu Pro Pro Lys Asp Tyr Arg Ile Pro Leu Asn Pro Tyr Leu Asn Leu
 65                  70                  75                  80

His Ser Leu Leu Pro Ala Ser Asn Leu Ala Gly Lys Glu Ala Arg Gly
                 85                  90                  95

Trp Gly Ala Gly Arg Ser Arg Arg Pro Ala Glu Gly Pro Pro Thr
            100                 105                 110

Asn Pro Pro Ala Pro Gly Gly Gly Ser Ser Ser Lys Ala Phe Gln
            115                 120                 125

Leu Lys Ser Arg Leu Leu Ser Pro Leu Ser Ser Ala Arg Leu Pro Pro
130                 135                 140

Glu Pro Gly Leu Ser Asp Ser Tyr Ser Phe Asp Tyr Pro Ser Asp Met
145                 150                 155                 160

Gly Pro Arg Arg Leu Phe Ser His Pro Arg Glu Pro Ala Leu Gly Pro
                165                 170                 175

His Gly Pro Ser Arg His Lys Met Ser Pro Pro Ser Gly Phe Gly
                180                 185                 190

Glu Arg

<210> SEQ ID NO 5
<211> LENGTH: 50
<212> TYPE: RNA
<213> ORGANISM: Unknown
<220> FEATURE:
<223> OTHER INFORMATION: Description of Unknown:
      RANBP1 cryptic exon sequence

<400> SEQUENCE: 5
acgugccucu gaacucagag caggcgccca ggcugggcuc gggacgagga            50

<210> SEQ ID NO 6
<211> LENGTH: 50
<212> TYPE: RNA
<213> ORGANISM: Unknown
<220> FEATURE:
<223> OTHER INFORMATION: Description of Unknown:
      ADAMT56 cryptic exon sequence

<400> SEQUENCE: 6
ggguccccaa ccauggccug uuaggccgca cagugggaag ucagcugcag            50

<210> SEQ ID NO 7
<211> LENGTH: 50
<212> TYPE: RNA
<213> ORGANISM: Unknown
<220> FEATURE:
<223> OTHER INFORMATION: Description of Unknown:
      ZC3H12C cryptic exon sequence

<400> SEQUENCE: 7
cuuaguaaau gguuguaaug ugguaaacug cugauauugc uucaacuaag            50

<210> SEQ ID NO 8
<211> LENGTH: 50
<212> TYPE: RNA
<213> ORGANISM: Unknown
```

```
<220> FEATURE:
<223> OTHER INFORMATION: Description of Unknown:
      PPP2R2D cryptic exon sequence

<400> SEQUENCE: 8
cgugggggua ugugugcagc auuucauaaa uuuuaaaugu uuaacuggau          50

<210> SEQ ID NO 9
<211> LENGTH: 50
<212> TYPE: RNA
<213> ORGANISM: Unknown
<220> FEATURE:
<223> OTHER INFORMATION: Description of Unknown:
      ZNF529 cryptic exon sequence

<400> SEQUENCE: 9
guuagugcua uuguuuacga cgucagugcu guuugaucgg acucaggacg          50

<210> SEQ ID NO 10
<211> LENGTH: 50
<212> TYPE: RNA
<213> ORGANISM: Unknown
<220> FEATURE:
<223> OTHER INFORMATION: Description of Unknown:
      USP13 cryptic exon sequence

<400> SEQUENCE: 10
gucagugagu gugcacggcu gcuagcuaga ugcgcauggc ucugugucag          50

<210> SEQ ID NO 11
<211> LENGTH: 49
<212> TYPE: RNA
<213> ORGANISM: Unknown
<220> FEATURE:
<223> OTHER INFORMATION: Description of Unknown:
      BIRC3 cryptic exon sequence

<400> SEQUENCE: 11
uguugccuaa auuccacaa auaugucucc ugaguagcug gaaauacag            49

<210> SEQ ID NO 12
<211> LENGTH: 50
<212> TYPE: RNA
<213> ORGANISM: Unknown
<220> FEATURE:
<223> OTHER INFORMATION: Description of Unknown:
      CD01 cryptic exon sequence

<400> SEQUENCE: 12
ucguggucgu gguuugcagu uuguugugge aguggugguhg guugguugug          50

<210> SEQ ID NO 13
<211> LENGTH: 50
<212> TYPE: RNA
<213> ORGANISM: Unknown
<220> FEATURE:
<223> OTHER INFORMATION: Description of Unknown:
      FAM114A2 cryptic exon sequence

<400> SEQUENCE: 13
guacuguggu acuacuuggu acguauacuu cuuaguuggu uuguauguca          50

<210> SEQ ID NO 14
<211> LENGTH: 50
<212> TYPE: RNA
<213> ORGANISM: Unknown
<220> FEATURE:
```

```
<223> OTHER INFORMATION: Description of Unknown:
      ACSF2 cryptic exon sequence

<400> SEQUENCE: 14
gccaugugug auuggaaggu ggcccguggu uggucagaca caaaccuggc          50

<210> SEQ ID NO 15
<211> LENGTH: 50
<212> TYPE: RNA
<213> ORGANISM: Unknown
<220> FEATURE:
<223> OTHER INFORMATION: Description of Unknown:
      CEP72 cryptic exon sequence

<400> SEQUENCE: 15
gcccuucaug cugucugucg cauguaugga cugugagaug ggacugugag          50

<210> SEQ ID NO 16
<211> LENGTH: 50
<212> TYPE: RNA
<213> ORGANISM: Unknown
<220> FEATURE:
<223> OTHER INFORMATION: Description of Unknown:
      PKN1 cryptic exon sequence

<400> SEQUENCE: 16
gacuggcccu gugagugaug guguuacugc ccuguauucc acgcucacag          50

<210> SEQ ID NO 17
<211> LENGTH: 49
<212> TYPE: RNA
<213> ORGANISM: Unknown
<220> FEATURE:
<223> OTHER INFORMATION: Description of Unknown:
      GPSM2 cryptic exon sequence

<400> SEQUENCE: 17
gguagagagu gagugugugu ugugugugua ugagagagag agcgaacag           49

<210> SEQ ID NO 18
<211> LENGTH: 50
<212> TYPE: RNA
<213> ORGANISM: Unknown
<220> FEATURE:
<223> OTHER INFORMATION: Description of Unknown:
      SLC39A8 cryptic exon sequence

<400> SEQUENCE: 18
gcacuccauu cuuauugcug ugugugugguu gaaagagaga gagagauuag          50

<210> SEQ ID NO 19
<211> LENGTH: 50
<212> TYPE: RNA
<213> ORGANISM: Unknown
<220> FEATURE:
<223> OTHER INFORMATION: Description of Unknown:
      XPO4 cryptic exon sequence

<400> SEQUENCE: 19
guuagcccau uguuggaggc ugacugcuga cugugugugu augugugugg          50

<210> SEQ ID NO 20
<211> LENGTH: 50
<212> TYPE: RNA
<213> ORGANISM: Unknown
<220> FEATURE:
<223> OTHER INFORMATION: Description of Unknown:
```

ST5 cryptic exon sequence

<400> SEQUENCE: 20
aguggaagcu ccuugaggau ggaccauauu agcugaaugg augcaugacu                50

<210> SEQ ID NO 21
<211> LENGTH: 50
<212> TYPE: RNA
<213> ORGANISM: Unknown
<220> FEATURE:
<223> OTHER INFORMATION: Description of Unknown:
      ACOT11 cryptic exon sequence

<400> SEQUENCE: 21
ggccggacac acacaagagg uggucugcug gaagaacugc aggaguguau                50

<210> SEQ ID NO 22
<211> LENGTH: 50
<212> TYPE: RNA
<213> ORGANISM: Unknown
<220> FEATURE:
<223> OTHER INFORMATION: Description of Unknown:
      SLC17A9 cryptic exon sequence

<400> SEQUENCE: 22
guaaggggag cucaggcggc ucccuucuag agcacagcug gaggccggug                50

<210> SEQ ID NO 23
<211> LENGTH: 50
<212> TYPE: RNA
<213> ORGANISM: Unknown
<220> FEATURE:
<223> OTHER INFORMATION: Description of Unknown:
      PFKP cryptic exon sequence

<400> SEQUENCE: 23
aaauaaucca aaucggugcc uccccgauaa gaugugaacg gagaguugaa                50

<210> SEQ ID NO 24
<211> LENGTH: 50
<212> TYPE: RNA
<213> ORGANISM: Unknown
<220> FEATURE:
<223> OTHER INFORMATION: Description of Unknown:
      HDGFRP2 cryptic exon sequence

<400> SEQUENCE: 24
gagcccacca ucugguuugg aaagggaggg acacagaaga gaggagagag                50

<210> SEQ ID NO 25
<211> LENGTH: 50
<212> TYPE: RNA
<213> ORGANISM: Unknown
<220> FEATURE:
<223> OTHER INFORMATION: Description of Unknown:
      BCL2L13 cryptic exon sequence

<400> SEQUENCE: 25
gcuggacuac aguggcacga ucauauccug aguugaguag augagacuac                50

<210> SEQ ID NO 26
<211> LENGTH: 50
<212> TYPE: RNA
<213> ORGANISM: Unknown
<220> FEATURE:
<223> OTHER INFORMATION: Description of Unknown:
      ZFP91 cryptic exon sequence

<210> SEQ ID NO 26
...

<400> SEQUENCE: 26
gcaaacagaa gaagaucaga uuaguaacau uucccaaucc uccaaaagaa           50

<210> SEQ ID NO 27
<211> LENGTH: 50
<212> TYPE: RNA
<213> ORGANISM: Unknown
<220> FEATURE:
<223> OTHER INFORMATION: Description of Unknown:
      RHEBL1 cryptic exon sequence

<400> SEQUENCE: 27
gugagucucc gcccugcaga gcucggcgag gauuggaaga guggaggaau           50

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgctcgaga ccatggcctc tgaatatatt cg                              32

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgtctagact accgttcgcc gaagccactt g                               31

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atctcgagat ggtgagcaag ggcgagga                                   28

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atctagacta tctattgcta ttgtgcttag gttcggc                         37

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 32
tgttgcatgt gtgagcgtgg                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctgttggag cgtttgatgt                                                    20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcgagccat tcacatacgc                                                    20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttcccacgca gacactcaca                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agttctgctg cgatcgcgcc                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagcaacaac aacagcacag                                                    20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```

```
ctagatcctc agtccgttaa c                                              21
```

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
ctgatcgata tcattgccaa ga                                             22
```

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
tgtgtgtgtt tgtgggagtg tg                                             22
```

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
gtgtcaggac cttaaaggcg gt                                             22
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
gcgcgttgtg gacgttaaga                                                20
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
gccgtactga agaaaaccca                                                20
```

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgcgataagt gcagagaaac ag                                              22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gctatggatg ggaattccgc at                                              22

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtgtgtgtg tgtgtgtgtg tgtgtgcac                                       29

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acctggtgct gggccatgat                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gaggggtgtt ggaaggctgt                                                 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
taccactccc cacacttcgt                                                 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctccaacgac agtggcatct                                                 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcttcctgag gacctccgtt                                           20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aagtgcgagg acttcgtgag                                           20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cagcgatctg tctgctttgc                                           20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aggtcggtgt gaacggattt g                                         21

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggggtcgttg atggcaaca                                            19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aagggagaat catggaccag                                           20

```
<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccgtaaggca tcattggact                                                   20

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aacttcaaga tctgacaccc tcccc                                             25

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggccctggct catcaagaac tg                                                22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcttacaatg cctggcgtgg tg                                                22

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgtggttgcg caccctaact ataa                                              24

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aagccctgac cctttagatt ccattt                                            26
```

```
<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aaaacgcctg gcgatccctg aac                                                23

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agtggacatg tggtggtaag aa                                                 22

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcttcaaaga atgacacgcc a                                                  21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cctgcgctaa agatgtcggt                                                    20

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atgccccttt ccaaaccaga t                                                  21

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tggtcagaca caaacctgg                                                     19

<210> SEQ ID NO 69
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
accgagatga ctgtggtcag                                                  20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggccttcaag agttcccaca                                                  20

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggattgggaa atgttactag atgg                                             24

<210> SEQ ID NO 72
<211> LENGTH: 27
<212> TYPE: DNA
<213> ORGANISM: Drosophila melanogaster

<400> SEQUENCE: 72
cttgttggtt gagacgtgtg tgtatgt                                          27

<210> SEQ ID NO 73
<211> LENGTH: 20
<212> TYPE: DNA
<213> ORGANISM: Drosophila melanogaster

<400> SEQUENCE: 73
atgtgtgtga gtgtgtgtgc                                                  20

<210> SEQ ID NO 74
<211> LENGTH: 34
<212> TYPE: DNA
<213> ORGANISM: Drosophila melanogaster

<400> SEQUENCE: 74
gccaacgaaa acaaaaaaaa aaaaacaaaa ctaa                                  34

<210> SEQ ID NO 75
<211> LENGTH: 100
<212> TYPE: DNA
<213> ORGANISM: Drosophila melanogaster

<400> SEQUENCE: 75
tattgatggc ggatacttct gggttactcg gtgtgtgtgt gtgtgtgtgt gtgtgcacac      60
aatcaactcg aattaaattc aataacataa ctcaatcatg                           100
```

<210> SEQ ID NO 76
<211> LENGTH: 18
<212> TYPE: DNA
<213> ORGANISM: Drosophila melanogaster

<400> SEQUENCE: 76
ttggcagatg ctcatgcg                                                 18

<210> SEQ ID NO 77
<211> LENGTH: 70
<212> TYPE: DNA
<213> ORGANISM: Drosophila melanogaster

<400> SEQUENCE: 77
ttcgccccgt gccccaagaa tttgtgagtg tgctagtgcg agaacgagtg tatgagtgtg    60
ggtgtgagtg                                                          70

<210> SEQ ID NO 78
<211> LENGTH: 13
<212> TYPE: DNA
<213> ORGANISM: Drosophila melanogaster

<400> SEQUENCE: 78
ctgttgttgc tct                                                      13

<210> SEQ ID NO 79
<211> LENGTH: 75
<212> TYPE: DNA
<213> ORGANISM: Drosophila melanogaster

<400> SEQUENCE: 79
aaaaaaaaac acccgactga cagtgtaaat aatgatgata atgtgtgcgt gagtgtgtgt    60
gtgtgtgagt gtctg                                                    75

<210> SEQ ID NO 80
<211> LENGTH: 20
<212> TYPE: DNA
<213> ORGANISM: Drosophila melanogaster

<400> SEQUENCE: 80
catacatgta agcaggccgc                                               20

<210> SEQ ID NO 81
<211> LENGTH: 12
<212> TYPE: DNA
<213> ORGANISM: Drosophila melanogaster

<400> SEQUENCE: 81
tgtttgtgtg cg                                                       12

<210> SEQ ID NO 82
<211> LENGTH: 28
<212> TYPE: DNA
<213> ORGANISM: Drosophila melanogaster

<400> SEQUENCE: 82
tgtgtgtgtt tgtgggagtg tgtgctgc                                      28

<210> SEQ ID NO 83
<211> LENGTH: 28
<212> TYPE: DNA
<213> ORGANISM: Drosophila melanogaster

```
<400> SEQUENCE: 83
ttggtgtgtg tgctgtggtg tggtgtgg                                              28
```